(12) United States Patent
Pagani et al.

(10) Patent No.: US 9,669,109 B1
(45) Date of Patent: Jun. 6, 2017

(54) MODIFIED HUMAN U1SNRNA MOLECULE, A GENE ENCODING FOR THE MODIFIED HUMAN U1SNRNA MOLECULE, AN EXPRESSION VECTOR INCLUDING THE GENE, AND THE USE THEREOF IN GENE THERAPY OF FAMILIAL DYSAUTONOMIA AND SPINAL MUSCULAR ATROPHY

(71) Applicant: Universita di Ferrara, Ferrara (IT)

(72) Inventors: Franco Pagani, Monfalcone (IT); Mirko Pinotti, Ferrara (IT)

(73) Assignee: UNIVERSITA DI FERRARA, Ferrara (IT)

(*) Notice: Subject to any disclaimer, the term of this patent is extended or adjusted under 35 U.S.C. 154(b) by 0 days.

(21) Appl. No.: 14/950,362

(22) Filed: Nov. 24, 2015

(51) Int. Cl.
  C07H 21/04 (2006.01)
  A61K 48/00 (2006.01)
  C12N 15/86 (2006.01)

(52) U.S. Cl.
  CPC .......... *A61K 48/0066* (2013.01); *C12N 15/86* (2013.01); *C12N 2750/14143* (2013.01)

(58) Field of Classification Search
  CPC .................................................... C07H 21/04
  See application file for complete search history.

(56) References Cited

U.S. PATENT DOCUMENTS

| 9,074,207 B2 | 7/2015 | Pagani et al. |
| 2002/0058287 A1 | 5/2002 | Graaf et al. |
| 2010/0087511 A1 | 4/2010 | Singh et al. |
| 2010/0216238 A1 | 8/2010 | Baker et al. |

FOREIGN PATENT DOCUMENTS

WO 2007/002390 A2 1/2007

OTHER PUBLICATIONS

Gorman, Linda, et al.: "Restoration of correct splicing of thalassemic beta-globin pre-mRNA by modified U1 snRNAs", Journal of Biological Chemistry, vol. 275, No. 46, Nov. 2000 (Nov. 2000), pp. 35914-35919.
Buratti, Emanuele, et al.: "SR protein-mediated inhibition of CFTR exon 9 inclusion: molecular characterization of the intronic splicing silencer", Nucleic Acids Research, vol. 35, No. 13, 2007, pp. 4359-4368.
Dhir, Ashish and Buratti, Emanuele: "Alternative splicing: role of pseudoexons in human disease and potential therapeutic strategies", FEBS Journal, vol. 277, No. 4, Feb. 2010 (Feb. 2010), pp. 841-855.
Kato, K., et al.: "Hyperstable U1snRNA complementary to the K-ras transcripts induces cell death in pancreatic cancer cells", British Journal of Cancer, vol. 87, No. 8, Oct. 7, 2002 (Oct. 7, 2002), pp. 898-904.
Incitti, Tania, et al.: "Exon skipping and duchenne muscular dystrophy therapy: Selection of the most active U1 snRNA-antisense able to induce Dystrophin exon 51 skipping", Molecular Therapy, vol. 18, No. 9, Sep. 1, 2010 (Sep. 1, 2010), pp. 1675-1682, DOI:10.1038/MT.2010.123 [retrieved on Jun. 15, 2010].
De Angelis, Fernanda Gabriella, et al.: "Chimeric snRNA molecules carrying antisense sequences against the splice junctions of exon 51 of the dystrophin pre-mRNA induce exon skipping and restoration of a dystrophin synthesis in Delta 48-50 DMD cells", Proceedings of the National Academy of Sciences of the United States (PNAS), vol. 99, No. 14, Jul. 9, 2002 (Jul. 9, 2002), pp. 9456-9461, DOI:DOI:10.1073/PNAS.142302299 [retrieved on Jun. 20, 2002].
Denti, Michela Alessandra, et al.: "Chimeric adeno-associated virus/antisense U1 small nuclear RNA effectively rescues dystrophin synthesis and muscle function by local treatment of mdx mice", Human Gene Therapy, vol. 17. No. 5. May 2006 (May 2006), pp. 565-574.
Garcia-Blanco, Mariano A., et al.: "Alternative splicing in disease and therapy", Nature Biotechnology, vol. 22, No. 5, May 2004 (May 2004), pp. 535-546.
Garcia-Blanco, Mariano A., et al.: "Alternative splicing in disease and therapy—Supplementary Information", May 2004 (May 2004), retrieved from the Internet: URL:http://www.nature.com/nbt/journal/v22/n5/suppinfo/nbt964_SI.html [retrieved on May 18, 2011].
Nlend Nlend, Rachel, et al.: "Repair of pre-mRNA splicing. Prospects for a therapy for Spinal Muscular Atrophy", RNA Biology, vol. 7, No. 4, Jul. 2010 (Jul. 2010), pp. 430-440.
Singh, Natalia N., et al.: "Modulating role of RNA structure in alternative splicing of a critical exon in the spinal muscular atrophy genes", Nucleic Acids Research, vol. 35, No. 2, Jan. 2007 (Jan. 2007), pp. 371-389.
Pagani, Franco, et al.: "A new type of mutation causes a splicing defect in ATM", Nature Genetics, vol. 30, No. 4, Apr. 2002 (Apr. 2002), pp. 426-429.
Lund, E., et al.: "True genes for human U-1 small nuclear RNA. Copy number, polymorphism and methylation", Journal of Biological Chemistry, vol. 259, No. 3, 1984, pp. 2013-2021.
Montgomery, R.A., et al.: "Inhibition of fibrillin 1 expression using U1 snRNA as a vehicle for the presentation of antisense targeting sequence", Human Molecular Genetics, vol. 6, No. 4, 1997, pp. 519-525.
Le Roy, F., et al.: "RNA-targeting approaches for neuromuscular diseases", Trends in Molecular Medicine, vol. 15, No. 12, Dec. 2009 (Dec. 2009), pp. 580-591.

(Continued)

*Primary Examiner* — Kimberly Chong
(74) *Attorney, Agent, or Firm* — Lucas & Mercanti, LLP

(57) ABSTRACT

The invention provides a modified human U1snRNA molecule, capable of correcting the skipping of an exon caused by a mutation localized in the sequence comprised between 50 base pairs upstream and 20 base pairs downstream of an exon, wherein a portion of a single-stranded nucleotide sequence of the 5' region of the wild-type human U1snRNA is replaced by a single-stranded binding nucleotide sequence, wherein the binding nucleotide sequence is selected from the group consisting of: uggcgcuua, aauggcgcu, aguacaauggcgc (SEQ ID NO: 87), gcaaacaguacaau (SEQ ID NO: 88), ucgcaaacaguaca (SEQ ID NO: 89), gcaaacagu, cuagucgcaaac (SEQ ID NO: 90), uacaaaaguaagauuca (SEQ ID NO: 83), aaaccauaaaguuuuacaa (SEQ ID NO: 84) and caaaccauaaaguuuua (SEQ ID NO: 96).

16 Claims, 18 Drawing Sheets

(56) References Cited

OTHER PUBLICATIONS

Alanis, E., et al.: "An exon-specific U1 small nuclear RNA (snRNA) strategy to correct splicing defects", Human Molecular Genetics, 2012, pp. 2389-2398.

Mas, A., et al.: "Improvement of SMN2 Pre-mRNA Processing Mediated by Exon-Specific U1 Small Nuclear RNA", The American Journal of Human Genetics, vol. 96, Jan. 2015, pp. 93-103.

Carmel, I., et al.: "Comparative analysis detects dependencies among the 5' splice-site positions", RNA Society, vol. 10, No. 5, 2004, pp. 828-840.

Anderson, S., et al.: "Family Dysautonomia is Caused by Mutations of the IKAP Gene", Am. J. Hum.Genet, vol. 68, 2001, pp. 753-758.

Slaugenhaupt, S., et al.: "Tissue-Specific Expression of a Splicing Mutation in the IKBKAP Gene Causes Familial Dysautonomia", Am. J. Hum.Genet, vol. 68, 2001, pp. 598-605.

International Search Report based on International Application No. PCT/IB2011/054573 mailed Mar. 29, 2012. (7 pages).

Balestra, D., et al.: "Regulation of a strong F9 cryptic 5'ss by intrinsic elements and by combination of tailored U1snRNAs with antisense oligonucleotides", Human Molecular Genetics, vol. 24, No. 17, 2015, pp. 4809-4816.

Balestra, D., et al.: "An engineered U1 small nuclear RNA rescues splicing-defective coagulation F7 gene expression in mice", Journal of Thrombosis and Haemostasis, vol. 12, 2014, pp. 177-185.

Marquis, J., et al: "Spinal Muscular Atrophy: SMN2 Pre-mRNA Splicing Corrected by a U7 snRNA Derivative Carrying a Splicing Enhancer Sequence", Molecular Therapy, vol. 15, No. 08, 2007, pp. 1479-1486.

Nizzardo, M., et al.: "Spinal muscular atrophy phenotype is ameliorated in human motor neurons by SMN increase via different novel RNA therapeutic approaches", Scientific Reports, 2015, pp. 1-13.

```
─── fix-7        ──── fix22
              ──── fix16
              ──── fix13
            ──── fix10
           ──── fix9
           ──── fix7
     ──── fix1                         ──── fix38
                                  ──── fix33         ──── fix63
CCAGCAGgtcataatctgaataagatttttaaagaaaatctgtatctgaaacttcagcatttaacaaacctacat
```

Figure 5

AAAGgtatgttctttgaatacttacttataatgctcatgctaaaat cf11

Figure 14

```
                                          IK 12
                                        IK 10L
                              IK 5
                      IK 4                        IK 19
                    IK 2            IK 15
  CAA gtaagtgccattgtactgtttgcgactagttagcttgtgatttatgtgtga
```

MODIFIED HUMAN U1SNRNA MOLECULE, A GENE ENCODING FOR THE MODIFIED HUMAN U1SNRNA MOLECULE, AN EXPRESSION VECTOR INCLUDING THE GENE, AND THE USE THEREOF IN GENE THERAPY OF FAMILIAL DYSAUTONOMIA AND SPINAL MUSCULAR ATROPHY

FIELD OF THE INVENTION

The present invention concerns modified human snRNA molecules (hereinafter designated as Exon Specific U1—ExSpeU1), which are suitable to be used in gene therapy methods. In particular, the invention relates to snRNA molecules capable of correcting aberrant splicing processes caused by genetic mutations and related to human diseases with different case histories, which are often very serious.

BACKGROUND OF THE INVENTION

Many human genetic diseases (about 15%) are caused by genetic mutations that, by interfering with the correct messenger RNA intracellular maturation, compromise the accurate subsequent protein biosynthesis and induce synthesis of non-functional proteins. Mostly, the point mutations accountable for splicing defects concern gene sequences that are critical for the recognition of the primary transcript by the machinery appointed for processing the same. The donor and acceptor sites located at the exon-intron boundaries, as well as gene-specific regulatory elements in exons or introns (Cartegni L et al., 2002; Pagani et al., 2004) are among the most significant sequences. As a consequence of these mutations, various molecular events, which most frequently concern the exclusion of one exon from the mature transcript, the so-called exon skipping, may be induced.

It has been known for a long time that molecular changes in the processing of messenger RNA, which involve, for instance, exon skipping, represent the main etiopathogenic mechanism of various human diseases, among which hemophilia B, cystic fibrosis, and spinal muscular atrophy and familial dysautonomia, which share the seriousness of their clinical courses. Different types of mutations can induce exon skipping, and specifically mutations in the donor site (or 5' splicing site), mutations in the acceptor site (3' splicing site), or exonic mutations. As examples of different types of mutations that induce exon skipping, following are described three models of human diseases.

The defect in the coagulation factor IX (FIX) accounts for the onset of hemophilia B, a disease accompanied by varying degrees of hemorrhagic manifestations, sometimes very serious and disabling. In some cases, the disease is caused by splicing defects. In particular, the exclusion of exon 5 from mRNA during the splicing process is caused both by mutations at position −2 within the exon 5 donor site of the factor IX gene (F9), and by mutations at positions −8 and −9 within the poly-pyrimidine sequence in the acceptor site.

The limitations of the current hemophilia B therapy, which is mainly based on the frequent infusion of recombinant exogenous FIX or of FIX directly derived from plasma, emphasize the need of developing alternative approaches that are characterized by a greater efficacy and a long-lasting effect.

Cystic fibrosis (CF) is the most frequent lethal congenital hereditary disease in the Caucasian population: one newborn out of 2500-2700 born-alive infants is affected by it.

The pathogenesis of this disease is secondary to an anomaly of a protein designated as CFTR (Cystic Fibrosis Transmembrane Conductance Regulator) localized in the apical membrane of epithelium cells and having the function of regulating the hydroelectrolytic exchanges.

As a consequence of CFTR modification, the transfer of salts through cell membranes is compromised, mainly causing a production of secretions that could be defined as "dehydrated": a sweat very rich in sodium and chlorine and a dense and viscous mucus that tends to obstruct the ducts, compromising the function of various organs and systems. In the course of several studies, many modifications in the CFTR gene sequence were identified as associated with cystic fibrosis, which induce exon skipping. In particular, skipping of exon 12 is caused both by mutations localized within the splicing donor site of the exon itself, and by exonic mutations.

Spinal muscular atrophy (SMA, OMIM 253300, 253550, and 253400) is a recessive autosomal neuromuscular disease characterized by degeneration of spinal marrow alpha motoneurons, with an estimated prevalence of 1/10,000 born. SMA is associated with clinical syndromes that range from extremely serious, with critical muscle hypotonia and weakness since birth, to milder forms in which the onset occurs later during childhood or adolescence. To date, no treatment for this disease, which generally leads to death at an age that depends on the seriousness of the case history, has yet been identified.

In 95% of cases, the disease is caused by absence of the SMN1 gene. In the human genome, there is a gene homologous to SMN1 called SMN2. However, expression of SMN2 is impaired by a synonymous mutation in the exon which results in an aberrant maturation of the messenger RNA with consequent skipping of exon 7 and inactivation of the gene itself. Approaches designed to increase the number of exon 7-containing SMN2 transcripts would therefore allow to apply a compensation therapy for the absence of the SMN1 gene thanks to the correct expression of SMN2, with considerable implications for a potential effective treatment for SMA.

Familial dysautonomia ("FD", Rilay-Day syndrome, OMIM 223900) is an autosomal recessive disorder that affects the sensory and autonomic nervous system. FD is a very common disease with a carrier frequency of 1 in 27 in the Ashkenazi Jewish population and of 1 in 18 in Ashkenazi Jews of Polish descent. This neuropathy is characterized by poor development and progressive degeneration of the sensory and autonomic nerves. FD patients show a large number of symptoms due to the loss of neuronal function, including gastrointestinal dysfunction, cardiovascular instability, recurrent pneumonia, decreased sensitivity to pain and temperature, vomiting crisis, and defective lacrimation. To date there is only palliative therapy.

FD is caused by mutations that affect the IKBKAP gene, inducing an aberrant processing of its pre-mRNA. This gene encodes the ikappaB kinase complex associated protein (IKAP), which has a molecular weight of 150 kDa. IKAP is also known as elongator protein 1 (ELP1) that is a component of the human Elongator complex, which is required for an efficient RNA Pol II transcriptional elongation. IKAP has also been associated with other cellular functions in addition to its role in transcription.

As of the present date, there are three known mutations related to FD: an intronic non-coding point mutation (IVS20+6 T>C, c.2204+6T>C, NM_003640.2) and two missense mutations (R696P and P914L). Among these three mutations, it has been found that more than 99% of FD patients are homozygous for the IVS20+6 T>C at the donor splice site of intron 20. This mutation causes exon 20 skipping leading to a frameshift that generates a premature termination codon (PTC) in exon 21 of IKBKAP mRNA. Interestingly, this mutation does not completely abolish the inclusion of exon 20, resulting in a minimal expression of the full-length IKAP protein. However, in neurons, this amount is not sufficient to support a physiological activity, leading to the pathological condition.

During the splicing process, the small nuclear RNAs (snRNAs) play a primary role as essential components of the spliceosome, the cell machinery appointed to mediate the entire mRNA maturation process. In particular, the small U1 RNA (U1snRNA), 164 ribonucleotides in length, is encoded by genes that occur in several copies within the human genome and represents the ribonucleic component of the nuclear particle U1snRNP. The U1snRNA molecules have a stem and loop tridimensional structure and within the 5' region they include a single-stranded sequence, generally 9 nucleotides in length, capable of binding by complementary base pairing the splicing donor site on the pre-mRNA molecule (Horowitz et al., 1994). FIG. 1 shows a schematic representation of the wild-type U1snRNA structure. The sequence in the 5' region capable of recognizing the splicing donor site is shown paired with the consensus sequence of the splicing donor site in the primary transcripts of eukaryotic genes. Such a sequence exhibits varying degrees of conservation and is located at the exon/intron junction. The recognition mediated by the U1snRNA 5' region is critical for defining the exon/intron junctions on the primary transcript and for a correct assembly of the spliceosome complex.

The increasing number of human genetic diseases associated with pre-mRNA splicing defects, and the frequent seriousness of the clinical course of the same, stimulated in the last few years the research for therapeutic molecules aimed at correcting splicing defects at the molecular level.

The use of modified U1snRNA molecules capable of inducing in vitro the correct inclusion of the exon and restoring the correct splicing of coagulation factor VII mRNA in case of mutations located at the 5'ss site is described in Pinotti M et al. 2008 and Pinotti M et al., 2009. The illustrated mechanism is based on the recognition and binding of the modified U1snRNA directly onto the 5' mutated splicing site. However, this method presents a certain degree of non-specificity of action of the therapeutic snRNA molecule towards the target gene, due to the relative conservation of the 5'ss sites and consequent risk of interfering with the maturation of transcripts generated from other functional wild-type genes. Moreover, it requires the use of a U1snRNA modified for each mutation in the 5'ss.

The present invention demonstrates that modified U1 snRNA molecules complementary to intron sequences downstream of the 5' splicing site (and herein defined as Exon Specific U1s, ExSpeU1), are capable of restoring, during the splicing process, the exon inclusion which was impaired by different types of mutations. In three different human genetic disease models of therapeutic interest (spinal muscular atrophy, hemophilia, and cystic fibrosis), co-owned U.S. patent application Ser. No. 13/878,355, filed on Apr. 8, 2013, and the work of Fernandez Alanis et al., 2012 demonstrated that a single ExSpeU1 or a group of ExSpeU1s are able to induce the inclusion of the corresponding exon for each disease model. In the work of Dal Mas et al., 2015, it was also shown the effect of the use of three specific ExSpeU1s (sm2, sm17 and sm21) in cellular and animal models of spinal muscular atrophy. In U.S. Ser. No. 13/878,355, it was shown that a single ExSpeU1 or a group of ExSpeU1s correct the exon skipping caused by mutations in the donor site, mutations in the poly-pyrimidine tract of the acceptor site, and mutations in regulatory exon sequences. The correction effectiveness obtained with the ExSpeU1s is the same as that described in the prior art, but it would guarantee a greater selectivity of action on the target gene transcript of therapeutic interest. The ExSpeU1 approach allows use of a single modified U1-snRNA for correcting a panel of different genetic mutations that cause exon skipping. Accordingly, there remains a need in the art for a solution for familial dysautonomia that is caused by exon skipping.

SUMMARY OF THE INVENTION

These and other objects are achieved by a modified human U1snRNA molecule as defined in claim 1. The modified human U1snRNA molecule is characterized in that a portion of the single-stranded nucleotide sequence in the 5' region of the wild-type human U1snRNA is replaced by a binding single-stranded nucleotide sequence capable of hybridizing to a target nucleotide sequence on the primary transcript of a target gene of therapeutic interest bearing a mutation which induces aberrant splicing. The target nucleotide sequence of the U1snRNA molecule is located in a region of the pre-mRNA comprised between 2 and 50 base pairs downstream of an exon/intron junction site (5'ss), provided that the target nucleotide sequence does not comprise said exon/intron junction site.

Compared to the prior art, the U1snRNA molecules subject of the invention have the advantage of performing a targeted and selective (exon-specific) action, as they bind target nucleotide sequences on the primary transcript localized within the intron regions flanking the splicing donor site, which exhibit a lower degree of conservation compared to the sequences of the exon/intron junction sites. It is however surprising that, though operating on target sequences that do not include the exon/intron junction site, the U1snRNA molecules of the invention are all the same capable of inducing inclusion of the exon in the presence of different types of mutations, including the exonic ones or those on the acceptor site.

Accordingly, the invention provides a modified human U1snRNA molecule, capable of correcting the skipping of an exon caused by a mutation localized in the sequence comprised between 50 base pairs upstream and 20 base pairs downstream of an exon, wherein a portion of the single-stranded nucleotide sequence of the 5' region of the wild-type human U1snRNA is replaced by a single-stranded binding nucleotide sequence, wherein the binding nucleotide sequence is selected from the group consisting of: uggcgcuua, aauggcgcu, aguacaauggcgc (SEQ ID NO: 87), gcaaacaguacaau (SEQ ID NO: 88), ucgcaaacaguaca (SEQ ID NO: 89), gcaaacagu, cuagucgcaaac (SEQ ID NO: 90), uacaaaaguaagauuca (SEQ ID NO: 83), aaaccauaaaguuuuacaa (SEQ ID NO: 84) and caaaccauaaaguuuua (SEQ ID NO: 96).

In another embodiment, the invention provides for an isolated gene encoding for a modified human U1snRNA molecule. Preferably, the isolated gene comprises a promoter sequence and a polyadenylation signal sequence. The promoter is preferably the endogenous promoter of the gene encoding for human U1snRNA. The invention also provides for an expression vector that includes the isolated gene. The expression vector is preferably an adeno-associated viral vector.

In a further embodiment, the invention provides for a pharmaceutical composition comprising a modified human U1snRNA molecule, a gene encoding the modified human U1snRNA molecule, and/or an expression vector encoding the modified human U1snRNA molecule. In certain embodiments, the pharmaceutical composition preferably further includes a pharmaceutically acceptable carrier.

In a still further embodiment, the invention provides a method of treating a genetic disease, including spinal muscular atrophy and familial dysautonomia, that is caused by or associated with exon skipping, the method comprising administering the inventive modified human U1snRNA molecule, a gene or expression vector encoding the inventive modified human U1snRNA molecule In yet a further embodiment, the invention provides an in vitro method to restore in a cultured cell the correct splicing of a target gene of therapeutic interest bearing a mutation which induces exon skipping, comprising transfecting the cultured cell with an inventive expression vector, wherein the target gene of therapeutic interest is the SMN gene or the IKBKAP gene.

BRIEF DESCRIPTION OF THE DRAWINGS

FIG. 5 illustrates localization of the binding sites on the modified U1snRNA employed for the correction of exon 5 splicing defects of the clotting factor IX gene. The sequence of exon 5 is indicated in capital letters, whereas the remaining sequence indicates the intron (SEQ ID NO: 54).

SMN sh25 acuuagaaugaaaacau (this is SEQ ID NO: 83, but written 3' to 5'),
SMN sh2 auucagacg
SMN sh40 auuuugaaauaccaaac (this is SEQ ID NO: 96, but written 3' to 5')
−1G−2G−3A ccucauuca
SMN sh37 aacauuuugaaauaccaa (this is nucleotides 2-19 of SEQ ID NO: 84, but written 3' to 5')

The localization of the modified SMN U1 snRNAs are illustrated with respect to the primary transcript of the SMN2 gene, SMB sh37:

AAGGAguaagucugccagcauuaugaaagugaaucuuacuuuu-guaaaacuuuaugguuugugaaaa caaa (SEQ ID NO: 104).

Figure 12:
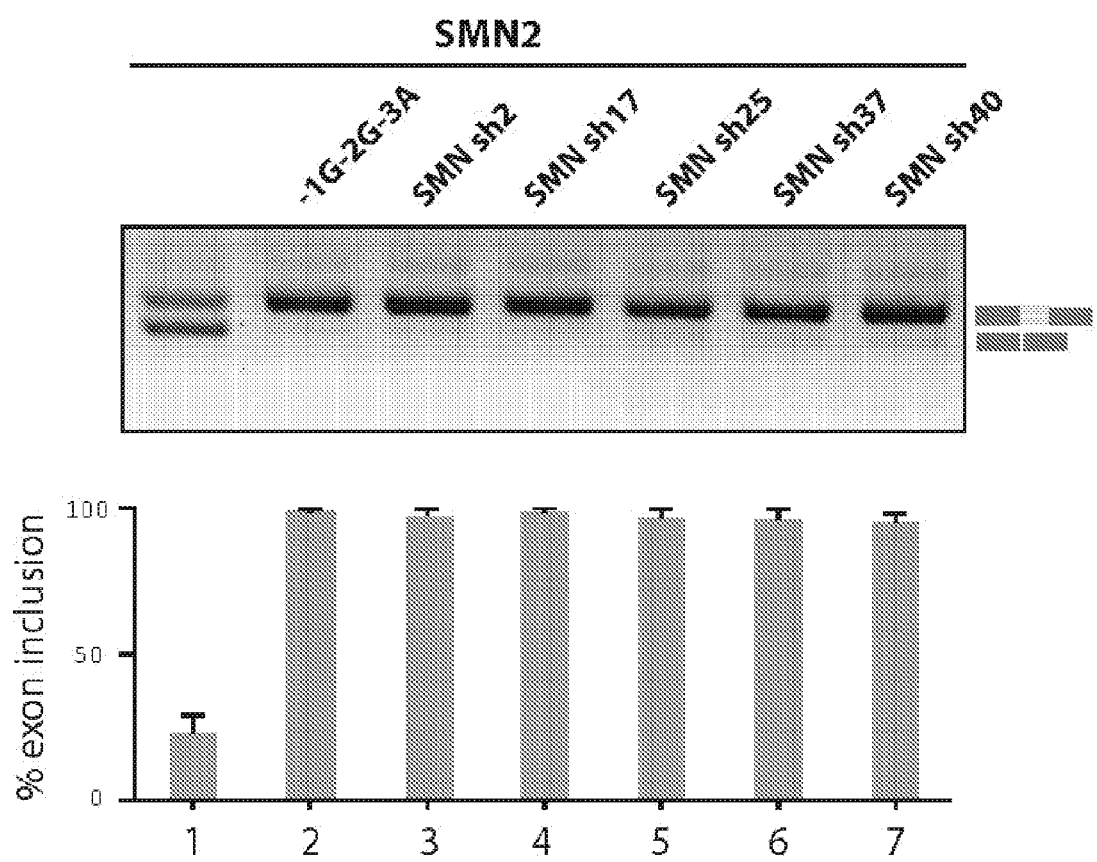

FIG. 12 illustrates the effect of modified SMN U1s on SMN2 splicing. The splicing profile of exon 7 of the SMN2 gene (lane 1) and the effect of co-expression of the modified U1 snRNAs (lanes 2-7) are indicated in the upper part of the figure. The two exon 7 inclusion (+) and exclusion (−) isoforms are indicated. In the lower panel the histogram shows the percentage of inclusion of exon 7, and thus, of the correct splicing. The data are the average of three independent experiments.

Figure 13:
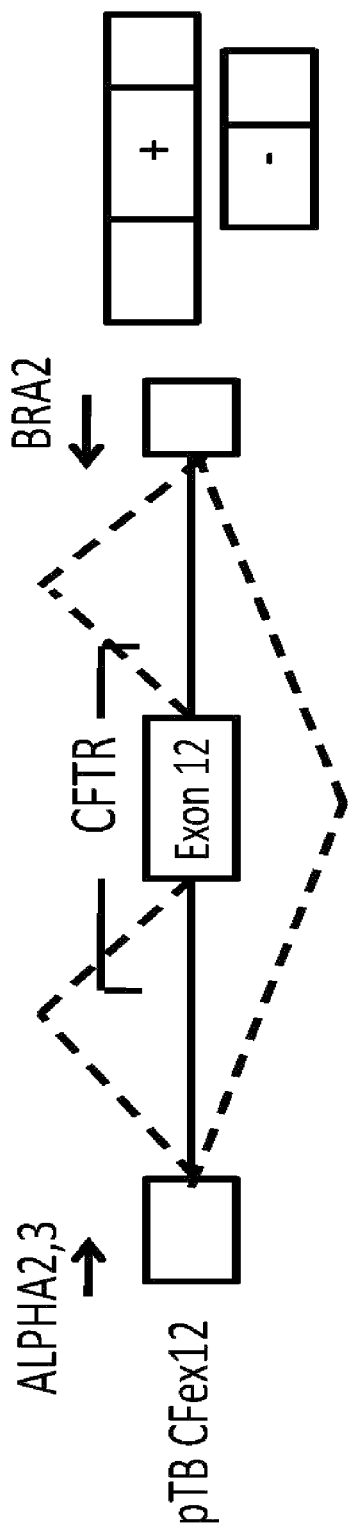

FIG. 13 schematically illustrates the pTB CFex12 minigene (Pagani et al., 2003). The rectangles represent the middle regions of the a-globin construct, and of the CFTR exon 12, with introns represented as lines. Exon 12 and the flanking intronic regions were cloned into plasmid pTB. The transcription is under the control of the a-globin promoter and SV 40 enhancer. The two possible splicing isoforms are indicated.

FIG. 14 schematically illustrates the localization of the ExSpeU1 ef1 1 that was used for correcting the splicing defects of exon 12 of the CFTR gene (SEQ ID NO: 55).

Figure 15:
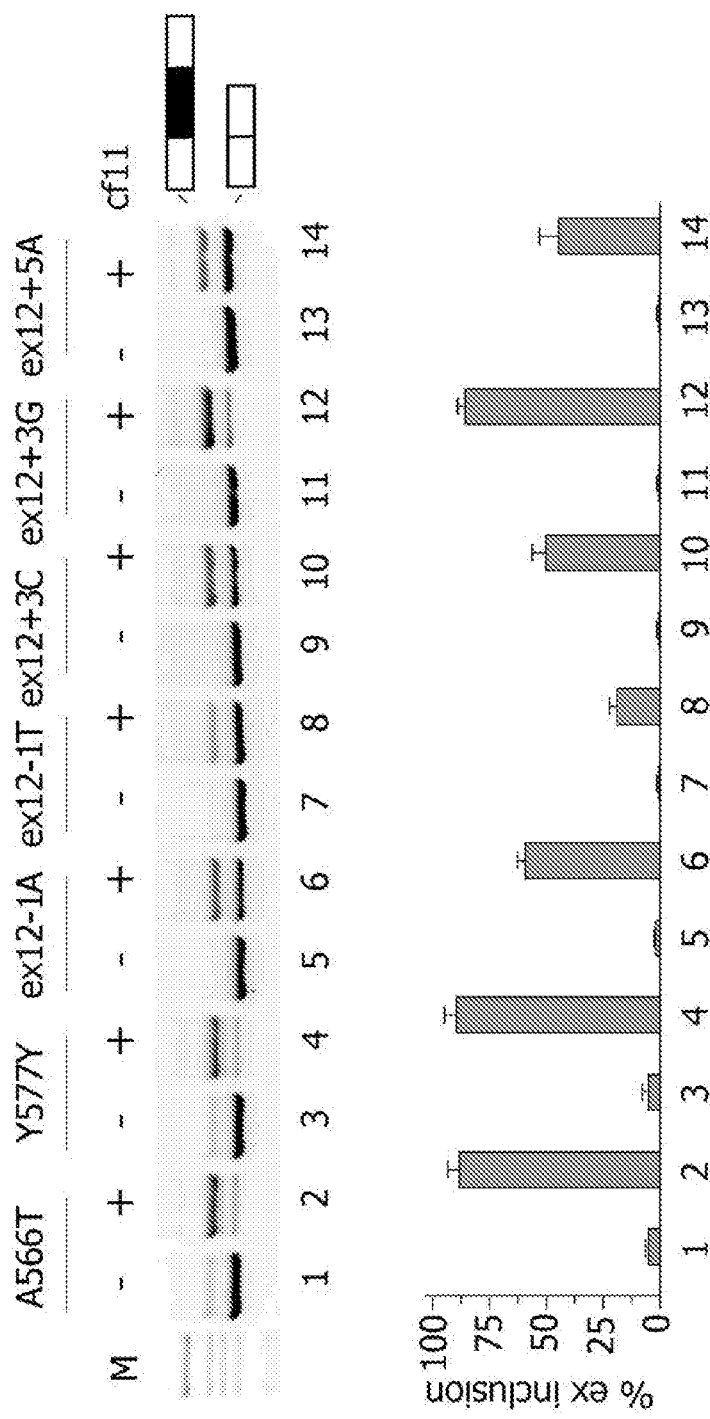

FIG. 15 illustrates the effect of ExSPeU1 cf1 1 on the aberrant splicing induced by different types of mutations localized in the 5'ss and in the exon. ExSPeU1 cf1 1 induces a significant increase in the percentage of inclusion of exon 12 in all the mutants analyzed.

Figure 16:
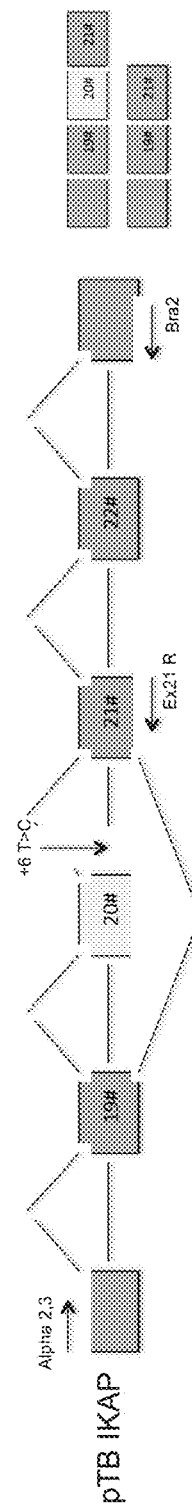

FIG. 16 schematically illustrates the pTB IKAP minigene including the genomic region of IKBKAP gene spanning intron 18 to intron 22. The rectangles represent the middle regions of the a-globin construct, and of the IKBKAP exons, with introns represented as lines. The IKBKAP genomic region was cloned into plasmid pTB. The IVS20+6T>C mutation is indicated. The transcription is under the control of the a-globin promoter and SV 40 enhancer. The normal and aberrant splicing patterns are indicated with dotted lines.

FIG. 17 illustrates the IKAP ExSpeU1s binding regions within the IKBKAP intron 20 (SEQ ID NO: 95).

Figure 18:
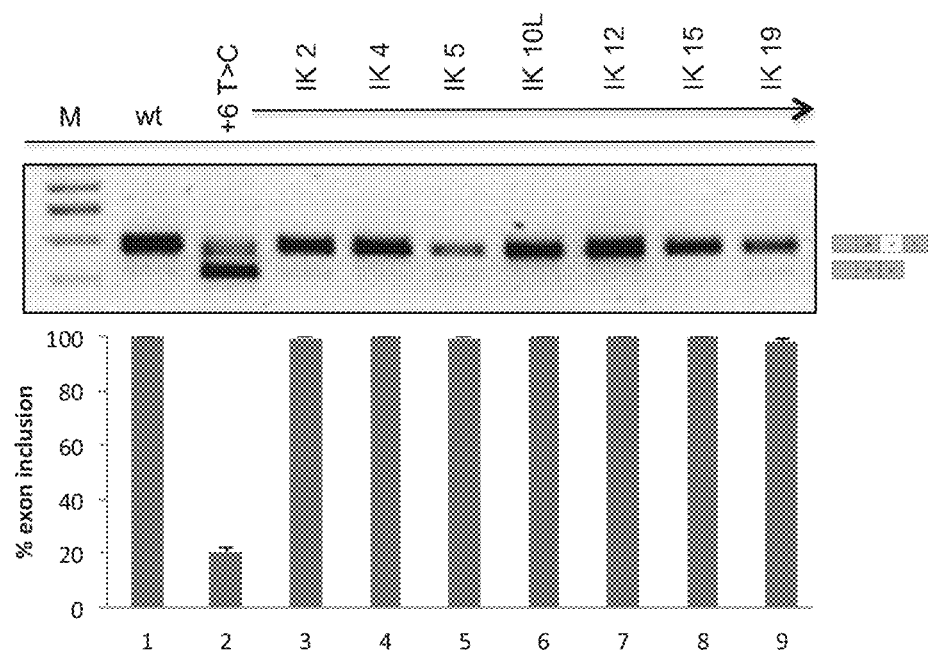

FIG. 18 illustrates the effects of the different IKAP ExSpeU1s on the aberrant splicing induced by the mutation causing familial dysautonomia. In the lower panel, the histograms report the % of exon 20 inclusion.

DETAILED DESCRIPTION OF THE INVENTION

Preferably, the mutations that are corrected by the ExSpeU1s and cause exon skipping are located in the sequence comprised between 3 and 50 base pairs upstream of an intron/exon junction site (3' splice site), exonic mutations and mutations within the consensus sequence of the splicing donor site.

The IKBKAP gene and the SMN gene are mentioned by way of example, among the genes of therapeutic interest, that is those bearing mutations related to diseases that lend themselves to treatment with the ExSpeU1s of the present invention.

In a preferred embodiment, the modified human U1snRNA molecule of the invention includes a binding nucleotide sequence selected from the group consisting of uggcgcuua, aauggcgcu, aguacaauggcgc (SEQ ID NO: 87), gcaaacaguacaau (SEQ ID NO: 88), ucgcaaacaguaca (SEQ ID NO: 89), gcaaacagu, cuagucgcaaac (SEQ ID NO: 90), uacaaaaguaagauuca (SEQ ID NO: 83), aaaccauaaaguuuua-caa (SEQ ID NO: 84) and caaaccauaaaguuuua (SEQ ID NO: 96).

In a preferred embodiment, the gene comprises a promoter sequence and a polyadenylation signal sequence. The inventors verified that the endogenous promoter of the gene encoding for human U1snRNA is particularly suitable, although other per se known promoters can also be used, which may easily be selected by a person of ordinary skill in the art.

The sequence of the forward strand of the wild-type human U1snRNA encoding gene (designated as SEQ ID NO: 5 in the sequence listing) is reported hereinafter by way of example, wherein the portion of the single-stranded 5' region which in the modified U1snRNA molecule is replaced by the binding sequence is in bold. The sequences of the unique BglII and BclI restriction sites, used for inserting the binding sequences, are underlined. In addition to the RNA encoding region, which is shown in capital letters, the SEQ ID NO: 5 gene sequence also comprises some regulatory elements required for its expression, such as the promoter and the polyadenylation signal.

(SEQ ID NO: 5)
5'- taaggaccagcttctttgggagagaacagacgcagggcgggagggaaaa agggagaggcagacgtcacttcccttggcggctctggcagcagattggt cggttgagtggcagaaaggcagacggggactgggcaaggcactgtcggtg acatcacggacagggcgacttctatgtagatgaggcagcgcagaggctga cgtcttcgccacttgctgcttcaccacgaaggagttcccgtgccctggga gcgggttcaggaccgctgatcggaagtgagaatcccagctgtgtgtcagg gctggaaagggctcgggagtgcgcggggcaagtgaccgtgtgtgtaaaga gtgaggcgtatgaggctgtgtcggggcagaggcccaagatctgATACTTA

CCTGGCAGGGGAGATACCATGATCACGAAGGTGGTTTTCCCAGGGCGAGG

CTTATCCATTGCACTCCGGATGTGCTGACCCCTGCGATTTCCCCAAATGT

-continued
GGGAAACTCGACTGCATAATTTGTGGTAGTGGGGGACTGCGTTCGCGCTT

TCCCCTGactttctggagtttcaaaagtagactgtacgctaa-3'.

Obviously, the above gene sequence is provided solely by way of example. Alternatively, in order to construct the gene encoding for the modified U1snRNAs of the invention, any gene sequence homologous to SEQ ID NO: 5 can be used, that is one able to encode for a U1snRNA capable of effectively mediating the recognition of the splicing donor site.

The preparation method for the different modified U1snRNA molecules subject of the invention, which contain the different binding sequences, is described in detail in the section of the Examples.

Still another object of the invention is an expression vector comprising an isolated gene as defined previously. The mostly preferred expression vector is an adeno-associated viral vector, although other types of expression vectors, which are per se known to a person of ordinary skill in the art, may also be used.

As previously described, the modified human U1snRNA molecule, the gene encoding for such an RNA molecule, and the vector including said gene are suitable to be used for the therapeutic treatment of a genetic disease caused by or associated with an aberrant splicing and characterized by exon skipping. Preferably, the disease is familial dysautonomia or spinal muscular atrophy.

In particular, it is an object of the invention a method of treating familial dysautonomia comprising administering a modified human U1snRNA molecule including a binding nucleotide sequence selected from the group consisting of uggcgcuua, aauggcgcu, aguacaauggcgc (SEQ ID NO: 87), gcaaacaguacaau (SEQ ID NO: 88), ucgcaaacaguaca (SEQ ID NO: 89), gcaaacagu, cuagucgcaaac (SEQ ID NO: 90), the gene encoding for such molecule or the vector including said gene to a patient in need thereof thereby treating the disease.

It is also an object of the invention a method of treating spinal muscular atrophy comprising administering a modified human U1snRNA molecule including a binding nucleotide sequence selected from the group consisting of uacaaaaguaagauuca (SEQ ID NO: 83), aaaccauaaaguuuua-caa (SEQ ID NO: 84) and caaaccauaaaguuuua (SEQ ID NO: 96), the gene encoding for such molecule or the vector including said gene to a patient in need thereof thereby treating the disease.

Said molecules, genes and/or vectors can be administered to a subject in need thereof by conventional methods. For example, intravenous administration may be used but other forms are equally suitable for carrying out the present invention.

Preferably, the molecules, genes and/or vectors of the invention are used in gene therapy, wherein nucleic acid molecules are delivered into patient's cells as a drug to treat a disease. Gene therapy can be performed according to methodologies well known in the art. In particular, suitable viral vectors may be used to deliver the molecules into the cells. Adeno-associated viral vectors are preferred. These are well known vectors for gene therapy.

The person skilled in the art will decide the effective doses and time of administration, depending on the patient's conditions, degree of severity of the disease, response of the patient and any other clinical parameter within the general knowledge of this matter. Reference can be made to Remington's Pharmaceutical Sciences Handbook, last edition.

To that end, the modified U1snRNA molecule, the gene and/or the vector are formulated into a pharmaceutical composition comprising, in addition to the therapeutically active molecules, a pharmaceutically acceptable carrier and/or excipient. For example, formulation coadjuvants, e.g. solubilizing agents, dispersing agents, suspension agents, and emulsifying agents can be used as carriers or excipients. The selection of the carrier and of the optional pharmaceutical excipients is well within the skill of a person of ordinary skill in the art. Average quantities of the active ingredient in the pharmaceutical composition may vary and in particular should be based upon the recommendations and prescription of a qualified physician.

Another aspect of the invention is an in vitro method for restoring, in a cultured cell, the correct splicing of a target gene of therapeutic interest bearing a mutation that induces an aberrant splicing, by transfecting the cultured cell with an expression vector as defined previously.

The modified U1snRNA molecules subject of the invention were generated by using conventional molecular biology methods which are well known to a person of ordinary skill in the art. To evaluate the effects of the U1snRNAs subject of the invention on the correction of the aberrant splicing processes, and for identifying the most efficient ones, the inventors extensively used the minigene method, the application of which has been widely documented in the scientific literature. Such a method comprises cloning a gene portion bearing the mutation that causes the splicing defects into an expression vector and then transfecting the recombinant vector into in vitro cultured cells. The analysis of the transcripts originated from the portion of the gene of interest is carried out by RT-PCR, thus allowing for the identification of mRNA molecules abnormal in length derived from the aberrant splicing processes. The appearance of transcripts of interest normal in length following co-transfection of the modified U1snRNAs with the minigenes, and the sequencing thereof, represents a clear indication of the ability of the U1snRNA molecules to restore correct splicing processes.

However, the analogy between the restoration of the correct messenger RNA processing and the restoration of the final protein levels, which have the actual therapeutic significance, is not obvious.

For this reason, the inventors used the hybrid minigene method which allows for the study of the splicing, but also of the expressed protein. This method was introduced by the inventors to study a splicing mutation in the coagulation FVII (Pinotti et al., 2009). Such a method comprises cloning into an expression vector a portion of a gene containing a few introns in the region bearing the mutation that causes the splicing defect, within the entire coding sequence ("splicing-competent cDNA construct"), and subsequently transfecting the recombinant vector into in vitro cultured cells. The analysis of the transcripts originated from the portion of the gene of interest by RT-PCR, and the measurement of the levels and activity of the synthesized protein allow for the assessment of the restoration of the biological function.

The following examples are provided by way of illustration and not of limitation of the scope of the invention as defined in the appended claims.

Example 1: Generation of the Modified U1 snRNAs

The modified U1 snRNAs were generated by the following procedure: the plasmid containing the sequence of the wild-type U1-snRNA gene, that is the non-modified U1-snRNA, was digested with the BglII and BclI restriction enzymes. The sequence comprised between these two restriction sites was replaced with a double-stranded oligonucleotide comprising the binding sequence. The direct and reverse sequences of each oligonucleotide are described in Table 1 below and the resulting modified U1-snRNAs are named after the employed oligonucleotides.

Figure 1:
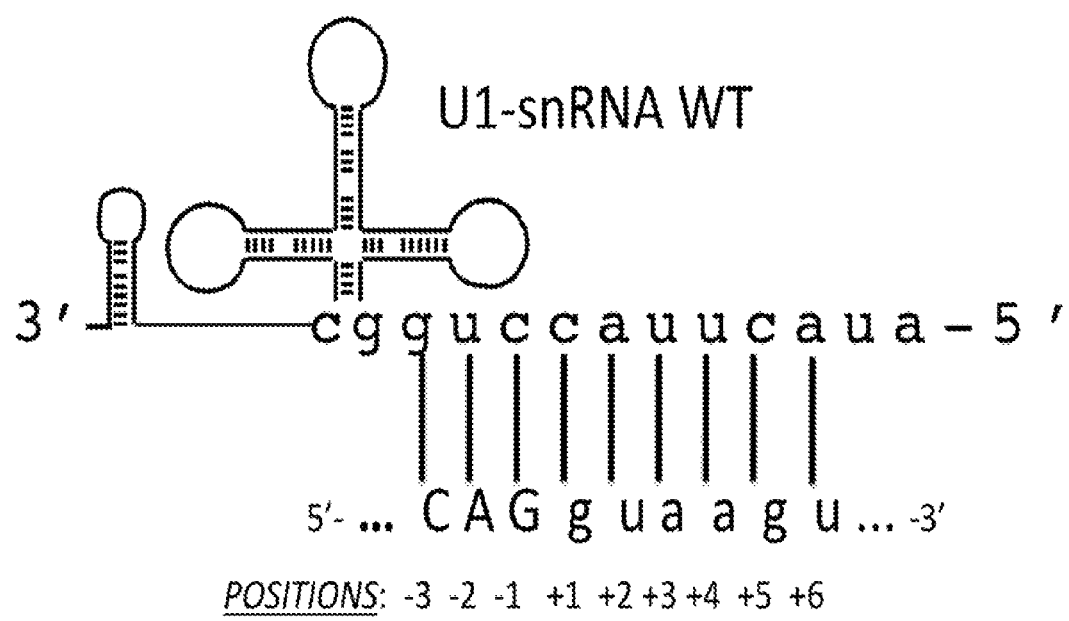
FIG. 1 illustrates a schematic representation of the wild-type U1snRNA structure. The sequence in the 5' region capable of recognizing the splicing donor site (SEQ ID NO: 51) is shown paired with the consensus sequence of the splicing donor site in the primary transcripts of eukaryotic genes.
Figure 2:
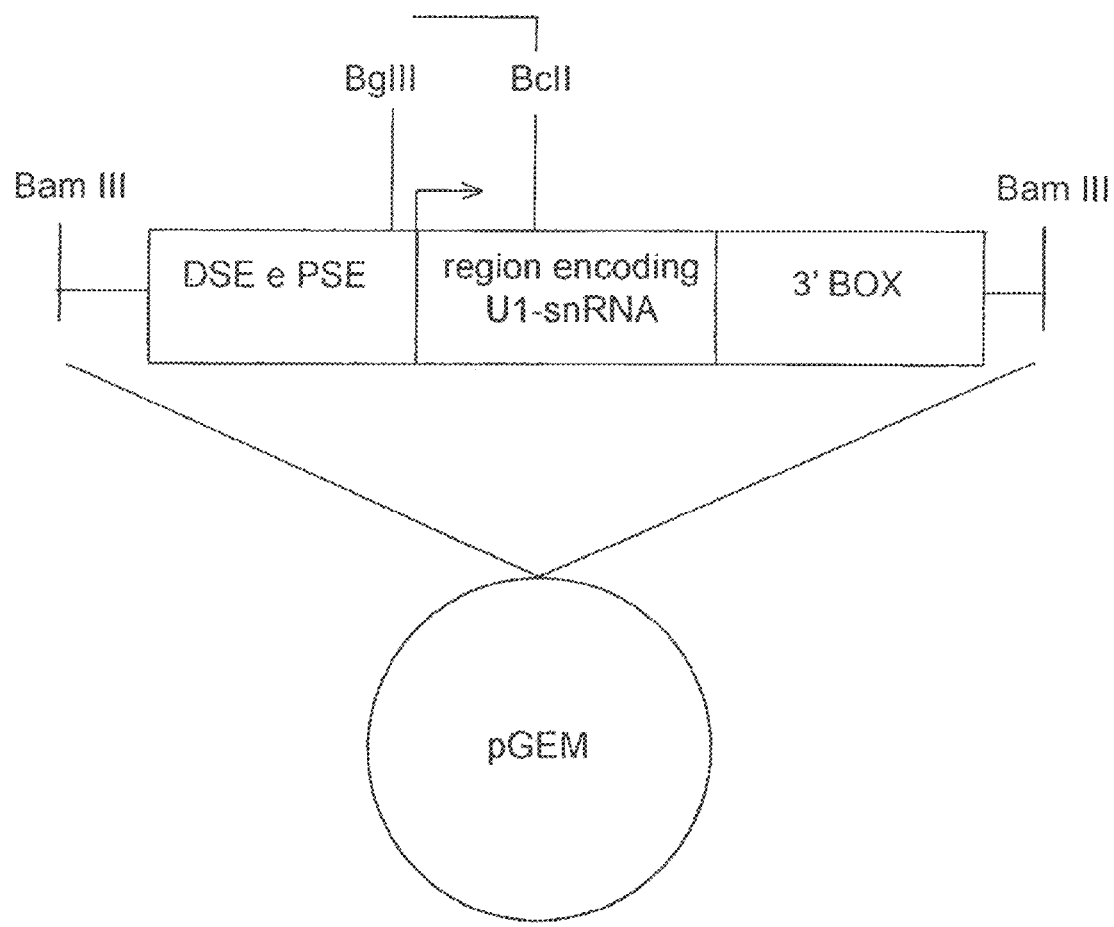
FIG. 2 illustrates the U1snRNA gene with the promoter elements DSE and PSE, the region encoding for U1snRNA (in the middle), and the 3' processing box, inserted in a plasmid vector (pGEM). The transcription start site is indicated by an arrow. The sequence between the BglII and BclI restriction sites includes the region encoding for the single stranded U1snRNA tail which has been replaced by oligonucleotides that are specific for generating the modified U1 snRNAs as indicated in Table 1.

Furthermore, FIG. 2 shows a schematic representation of the U1 snRNA gene elements. The cloning strategy by which the different modified U1 snRNAs were prepared is indicated. FIG. 2 shows the U1snRNA gene with the promoter elements DSE and PSE, the region encoding for U1 snRNA (in the middle), and the 3' processing box, inserted in a plasmid vector (pGEM). The transcription start site is indicated by an arrow. The sequence between the BglII and BclI restriction sites includes the region encoding for the single-stranded U1snRNA tail which has been replaced by oligonucleotides that are specific for generating the modified U1 snRNAs indicated in Table 1.

TABLE 1

|  |  | SEQ ID NO: |
|---|---|---|
| Oligonucleotides for U1 FIX exon 5 | | |
| FIX U1ex5 C3T5A6 dir | GATCTCattatgacctgGCAGGGGAGATACCAT | 6 |
| FIX U1ex5 C3T5A6 rev | gatcatggtatctcccctgccaggtcataatga | 7 |
| U1FIXex5 SH-7 dir | gatctcatatgacctgctgggcaggggagataccat | 8 |
| U1FIXex5 SH-7 rev | gatcatggtatctcccctgcccagcaggtcatatga | 9 |
| U1FIXex5 SH1 dir | gatctcatagattatgacgcaggggagataccat | 10 |
| U1FIXex5 SH1 rev | gatcatggtatctcccctgcgtcataatctatga | 11 |
| U1FIXex5 SH7 dir | gatctcatcttattcagatgcaggggagataccat | 12 |
| U1FIXex5 SH7 rev | gatcatggtatctcccctgcatctgaataagatga | 13 |
| U1FIXex5 SH9 dir | gatctcattcttattcaggcaggggagataccat | 14 |
| U1FIXex5 SH9 rev | gatcatggtatctcccctgcctgaataagaatga | 15 |
| U1FIXex5 SH10 dir | gatctcatatcttattcagcaggggagataccat | 16 |
| U1FIXex5 SH10 rev | gatcatggtatctcccctgctgaataagatatga | 17 |
| U1FIXex5 SH13 dir | gatctcataaaatcttatgcaggggagataccat | 18 |
| U1FIXex5 SH13 rev | gatcatggtatctcccctgcataagatttatga | 19 |
| U1FIXex5 SH16 dir | gatctcatataaaaaatctgcaggggagataccat | 20 |
| U1FIXex5 SH16 rev | gatcatggtatctcccctgcagattttatatga | 21 |
| U1FIXex5 SH22 dir | gatctcatatttctttaaagcaggggagataccat | 22 |
| U1FIXex5 SH22 rev | gatcatggtatctcccctgctttaaagaaatatga | 23 |
| U1FIXex5 SH33 dir | gatctcattcagatacagagcaggggagataccat | 24 |
| U1FIXex5 SH33 rev | gatcatggtatctcccctgctctgtatctgaatga | 25 |

TABLE 1-continued

| | | SEQ ID NO: |
|---|---|---|
| U1FIXex5 SH38 dir | gatctcatagtttcagatgcaggggagataccat | 26 |
| U1FIXex5 SH38 rev | gatcatggtatctcccctgcatctgaaactatga | 27 |
| U1FIXex5 SH63 dir | gatctcatttatgtaggtgcaggggagataccat | 28 |
| U1FIXex5 SH63 rev | gatcatggtatctcccctgcacctacataaatga | 29 |
| Oligonucleotides for U1 SMN | | |
| U1ex7SMN-1G-2G-3A rev | gat cat ggt atc tcc cct gcg gag taa gtt atg a | 30 |
| U1ex7SMN-1G-2G-3A dir | gat ctc ata act tac tcc gca ggg gag ata cca t | 31 |
| U1ex7SMN sh2 rev | gat cat ggt atc tcc cct gct aag tct gct atg a | 32 |
| U1ex7SMN sh2 dir | gat ctc ata gca gac tta gca ggg gag ata cca t | 33 |
| U1ex7SMN sh17 rev | gat cat ggt atc tcc cct gct atg aaa gtt atg a | 34 |
| U1ex7SMN sh17 dir | gat ctc ata act ttc ata gca ggg gag ata cca t | 35 |
| U1ex7SMN sh25 dir | gatctcATATACAAAAGTAAGATTCAgcaggggagataccat | 97 |
| U1ex7SMN sh25 rev | gatcatggtatctcccctgcTGAATCTTACTTTTGTATATga | 98 |
| U1ex7SMN sh37 dir | gatctcATAAACCATAAAGTTTTACAAgcaggggagataccat | 99 |
| U1ex7SMN sh37 rev | gatcatggtatctcccctgcTTGTAAAACTTTATGGTTTATga | 100 |
| U1ex7SMN sh40 dir | gatctcATACAAACCATAAAGTTTTAgcaggggagataccat | 101 |
| U1ex7SMN sh40 rev | gatcatggtatctcccctgcTAAAACTTTATGGTTTGTATga | 102 |
| Oligonucleotides for U1 CFTR exon 12 | | |
| U1-1A 4T dir | gatctcatacatacttggcaggggagataccat | 36 |
| U1-1A 4T rev | gatcatggtatctcccctgccaagtatgtatga | 37 |
| U1 G3 T4 dir | gatctcatacacacctggcaggggagataccat | 38 |
| U1 G3 T4 REV | gatcatggtatctcccctgccaggtgtgtatga | 39 |
| U1 T4 A5 dir | gatctcatatatacctggcaggggagataccat | 40 |
| U1 T4 A5 REV | gatcatggtatctcccctgccaggtatatatga | 41 |
| U1 CF sh+1 dir | gatctctcaaagaacatacgcaggggagataccat | 42 |
| U1 CF sh+1 REV | gatcatggtatctcccctgcgtatgttctttgaga | 43 |
| CF12 SH+9 Dir | gatctcataggtattcaaagcaggggagataccat | 44 |
| CF12 SH+9 Rev | gatcatggtatctcccctgctttgaatacctatga | 45 |
| CF12 SH+11 Dir | gatctcataagtaaggtattcagcaggggagataccat | 46 |
| CF12 SH+11 Rev | gatcatggtatctcccctgctgaataccttacttatga | 47 |
| CF12 SH+33 DIR | gatcatggtatctcccctgctcatgctaaaataga | 48 |
| CF12 SH+33 REV | gatctctattttagcatgagcaggggagataccat | 49 |
| Oligonucleotides for U1 IKBKAP | | |
| U1 IKBKAP sh2 dir | gatctcataTGGCGCTTAgcaggggagatac cat | 61 |
| U1 IKBKAP sh2 rev | gatcatggtatctcccctgcTAAGCGCCAtatga | 62 |
| U1 IKBKAP sh4 dir | gatctcataAATGGCGCTgcaggggagataccat | 63 |
| U1 IKBKAP sh4 rev | gatcatggtatctcccctgcAGCGCCATTtatga | 64 |
| U1 IKBKAP sh5 dir | gatctcataAGTACAATGGCGCgcaggggagataccat | 65 |
| U1 IKBKAP sh5 rev | gatcatggtatctcccctgcGCGCCATTGTACTtatga | 66 |
| U1 IKBKAP sh10L dir | gatctcataGCAAACAGTACAATgcaggggagataccat | 67 |
| U1 IKBKAP sh10L rev | gatcatggtatctcccctgcATTGTACTGTTTGCtatga | 68 |
| U1 IKBKAP sh12 dir | gatctcataTCGCAAACAGTACgcaggggagataccat | 69 |
| U1 IKBKAP sh12 rev | gatcatggtatctcccctgcTGTACTGTTTGCGAtatga | 70 |
| U1 IKBKAP sh15 dir | gatctcataGCAAACAGTgcaggggagataccat | 71 |
| U1 IKBKAP sh15 rev | gatcatggtatctcccctgcACTGT TTGCtatga | 72 |
| U1 IKBKAP sh19 dir | gatctcataCTAGTCGCAAACgcaggggagataccat | 73 |
| U1 IKBKAP sh19 rev | gatcatggtatctcccctgcGTTTGCGACTAGtatga | 74 |
| U1 IKBKAP sh33 dir | gatctcataATCACAAGCgcaggggagataccat | 75 |
| U1 IKBKAP sh33 rev | gatcatggtatctcccctgcGCTTGTGATtatga | 76 |

Example 2: Transfection of the Minigenes into Cultured Cells and Analysis of the Splicing Products The containing-vectors were inserted into the cells by transient transfection with Lipofectamine (liposomes). Following extraction of total cellular RNA with Trizol, the RNA was analyzed by RT-PCR with specific primers.

The reaction occurs in two steps: the RNA inverse transcription into a cDNA strand by a reverse transcriptase using random primers as templates, and amplification of the obtained cDNA by a DNA polymerase.

The PCR reaction was carried out in a final volume of 25 µl of a mixture containing:
  5 µl of AMV/Tfl 5× buffer suitable for the correct functioning of both the enzymes mentioned above;
  1 µl of 10 mM dNTPs mix;
  50 pmol of forward primer and 50 pmol of reverse primer;
  2 µl 25 mM MgSO$_4$;
  2 µl of cell-extracted RNA;
  1 µl of AMV-RT (0.1µ/µl), 1 µl of Tfl DNA polymerase;
  ultra pure H$_2$O q.s.

The reverse transcription step was performed at 45° C. for 45 min. A step wherein the PCR mix was adjusted to the temperature of 94° C. for 2 min was then carried out, followed by 40 rounds of PCR, and finally by an extension step for 7 sec at 68° C.

The amplification products were separated by electrophoresis in an agarose gel and/or run by capillary electrophoresis.

Example 3: Exonic Mutations Near the Donor Site and Mutations in the Poly-Pyrimidine Sequence Upstream of the Exon 5 Acceptor Site of the Coagulation Factor IX Associated with Hemophilia B In the factor IX gene (F9), the exonic mutations at position −2 within the donor site, as well as the mutations at positions −8 and −9 within the acceptor site of exon 5, are associated with hemophilia B. It is interesting to note that the mutations at position −2 in the exon are synonymous and do not modify the coding sequence but induce exon skipping and therefore they are classifiable as splicing mutations. The mutations at positions −8 and −9 within the acceptor site also induce skipping of exon 5.

Table 2 shows the mutations under discussion which were identified in patients affected by hemophilia B (Hemophilia B International database). Nucleotides belonging to exon 5 are shown in capital letters, whereas those belonging to the intron are in lower case. Each position, shown at the bottom of the figure, is affected by one or more mutations, the nucleotide change of which is shown in bold.

TABLE 2

| | Position | Nucleotide substitution | Sequence of the acceptor/donor site Positions: −12 to −1\ +1 to +6 |
|---|---|---|---|
| Acceptor site | −8 | T > G | tgctgcttttag\ATG (SEQ ID NO: 56) |
| | −9 | T > G | tgcgtcttttag\ATG (SEQ ID NO: 57) |
| Donor site | −2 | A > C | CCG\gtcata |
| | −2 | A > G | CGG\gtcata |
| | −2 | A > T | CTG\gtcata |

A vector for the expression of a minigene construct designated as pTB NdeI FIX was constructed to study the splicing of normal and mutated FIX. To do this, a portion of genomic DNA 308 bp upstream of exon 5 and 283 bp downstream of the region affected by the mutations was inserted into a vector widely used to study in vitro splicing, plasmid pTBNdeI (Pagani et al., 2000; Pagani et al 2002; Pagani et al., 2003).

Figure 3:
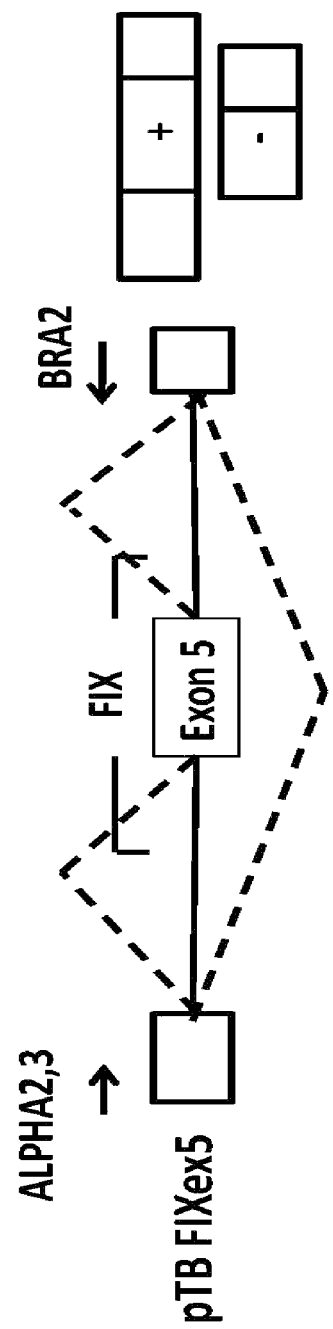
FIG. 3 schematically illustrates the middle portion of construct pTB FIX ex5 used for studying splicing.

In FIG. 3, the middle portion of construct pTB FIX ex5 used for studying splicing is represented schematically. The rectangles represent the middle regions of the construct of α globin and of FIX exon 5, with the introns represented as lines. Exon 5 and the flanking intronic regions (IVS4 and IVSS) were cloned into plasmid pTB. The transcription is under the control of the α globin promoter and of the SV40 enhancer. The two possible splicing isoforms are indicated.

Figure 4:
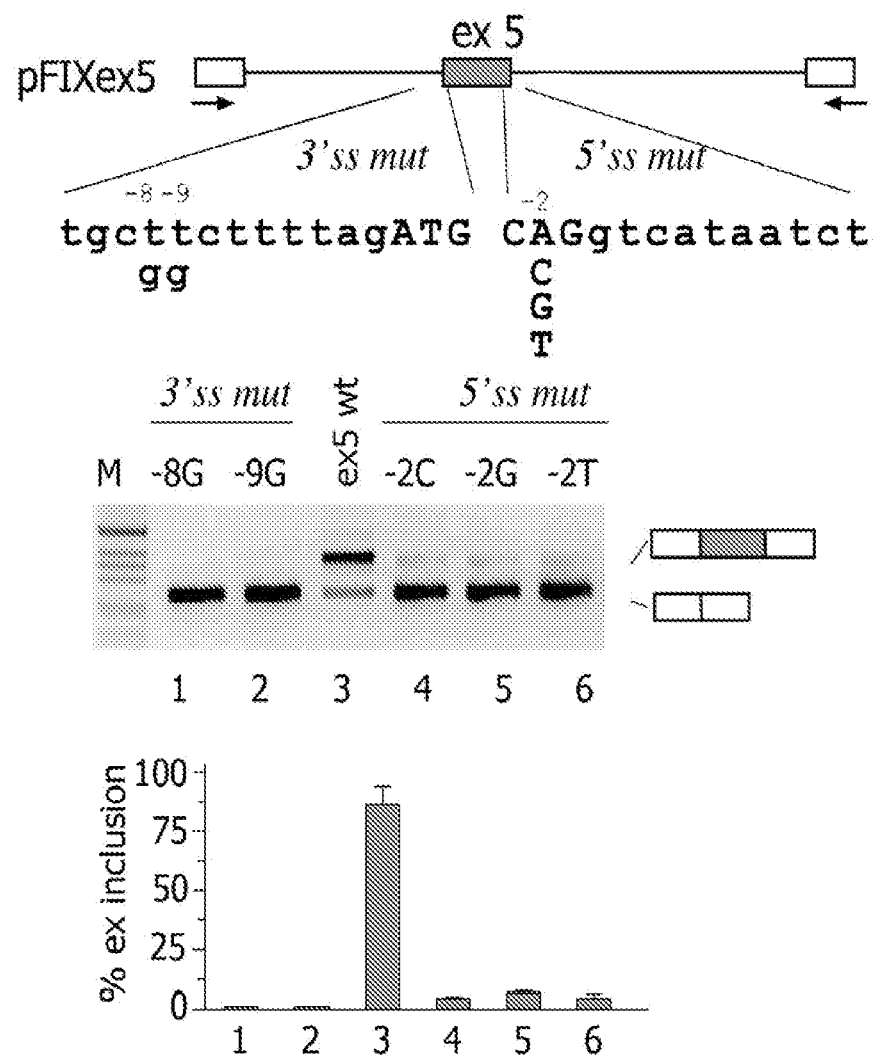
FIG. 4 illustrates the effects of the expression of minigenes generated in HepG2 eukaryotic cells. The vectors were inserted into the cells by transient transfection and the RNA was analyzed as indicated in the appended method, by using oligonucleotides alfa2-3 and BRA2 as the primers. The illustrated sequences represent the sequences of the acceptor/donor site, with possible mutation(s) as listed by Table 2, hereinbelow. The sequence on the left side of the figure is SEQ ID NO: 52. The sequence on the right side of the figure is SEQ ID NO: 53.

After inserting the mutations, the inventors have then demonstrated the causative effect thereof by the expression of minigenes generated in HepG2 eukaryotic cells, an ideal cell model for studying proteins of hepatic origin, such as FIX. In particular, the vectors were inserted into the cells by transient transfection and the RNA was analyzed as indicated in the appended method, by using oligonucleotides alfa2-3 and BRA2 as the primers. Specifically, all the mutations induce exon skipping (FIG. 4).

The list of the modified U1-snRNAs created, the target sequences thereof and the localization thereof around the donor site are reported in Table 3.

TABLE 3

Binding sequences of the modified U1-snRNAs for the correction of the splicing defects of exon 5 of the factor IX gene

| FIX U1 snRNAs | Binding sequence (5' -> 3') | Target sequence (5' → 3') | Length (bp) |
|---|---|---|---|
| C3T5A6 | uaugaccug | caggtcata | 9 |
| FIX-7 | ugaccugcugg (SEQ ID NO: 50) | ccagcaggtca (SEQ ID NO: 77) | 11 |
| FIX1 | agauuaugac (SEQ ID NO: 1) | gtcataatct (SEQ ID NO: 78) | 10 |
| FIX7 | ucuuauucaga (SEQ ID NO: 2) | tctgaataaga (SEQ ID NO: 79) | 11 |
| FIX9 | ucuuauuca | tgaataaga | 9 |
| FIX10 | aucuuauuc | gaataagat | 9 |
| FIX13 | aaaaucuua | taagatttt | 9 |
| FIX16 | uaaaaaauc | gattttta | 9 |
| FIX22 | uuucuuuaa | ttaaagaaa | 9 |
| FIX33 | auucagauacaga (SEQ ID NO: 58) | tctgtatctgaat (SEQ ID NO: 80) | 13 |
| FIX38 | auaguuucagau (SEQ ID NO: 59) | atctgaaactat (SEQ ID NO: 81) | 12 |
| FIX63 | auuuauguaggu (SEQ ID NO: 60) | acctacataaat (SEQ ID NO: 82) | 12 |

The localization of the binding sites on the modified U1 snRNAs employed for the correction of exon 5 splicing defects of the clotting factor IX gene is shown in FIG. 5. The sequence of exon 5 is indicated in capital letters, whereas the remaining sequence indicates the intron.

Figure 6:
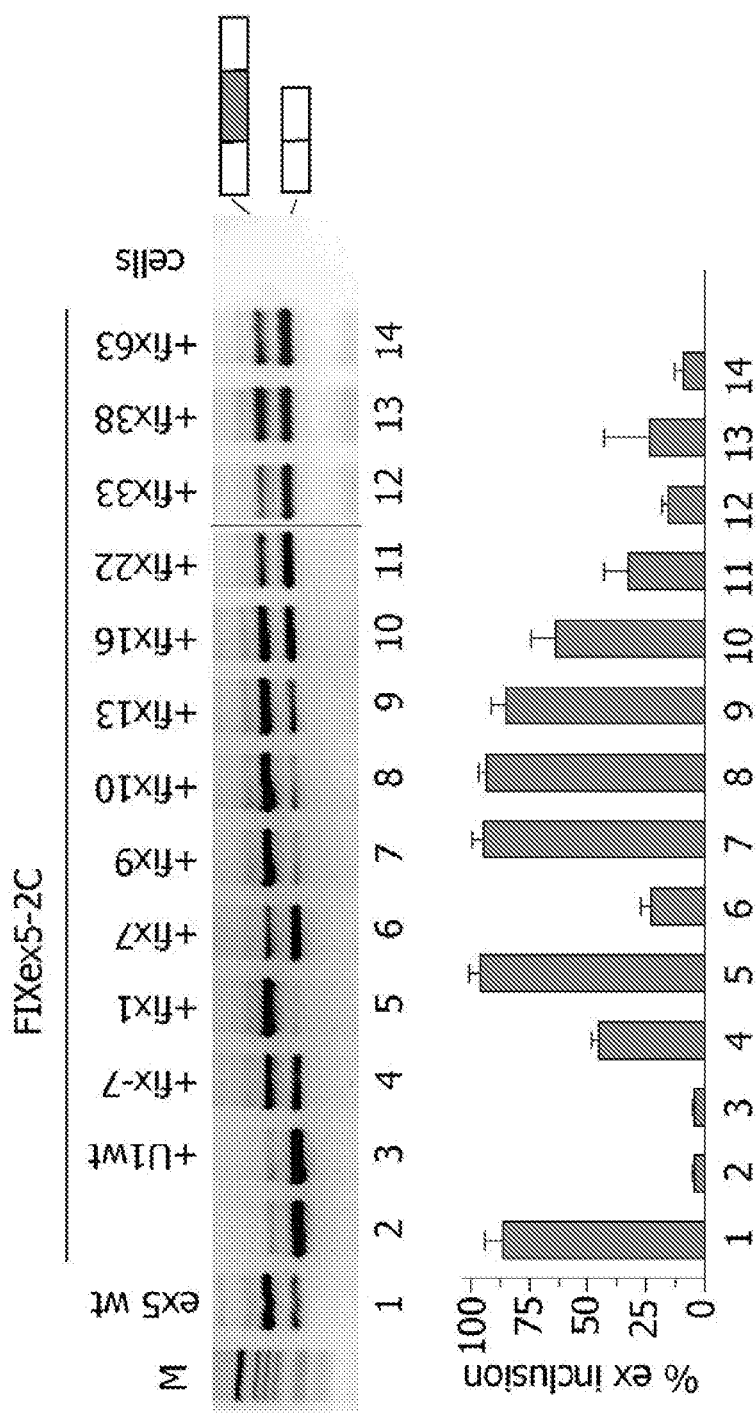
FIG. 6 illustrates different modified U1 snRNAs that were tested on the mutation at position −2C, and their effect on the percentage of exon 5 inclusion.

The different modified U1 snRNAs were tested on the mutation at position −2C, and their effect on the percentage of exon 5 inclusion is shown in FIG. 6. As can be observed, many modified U1 snRNAs are able to significantly increase the percentage of exon 5 inclusion, thereby compensating for the effects of the mutation at position −2C. This indicates that the binding of U1 snRNA to the donor site or nearby (ExSpeU1) favors the definition of exon 5. The efficiency depends on the position, and the U1-FIX1, FIX9, FIX10 show a higher activity. The efficiency decreases with increasing distance from the 5'ss splicing site. It is important to note that the U1 snRNA complementarity to non-conserved intronic sequences flanking the splicing site is important for increasing the specificity thereof. Moreover, it must be pointed out that even small increases in FIX (>2% of normal) would result in a significant improvement of patients' hemorrhagic tendency. For this reason, even the less efficient ExSpeU1 molecules may have a therapeutic significance in hemophilia B, as well as in other clotting defects. With the modified U1snRNA molecules analogous effects were achieved with the other mutations within the donor site (−2A>G, −2A>T) and the acceptor site (−8T>G, −9T>G).

Particularly noteworthy is the demonstration that one single modified U1snRNA, and particularly the one that pairs at position 9 (FIX9), is able to significantly restore splicing in the presence of all the different mutations investigated.

Figure 7:
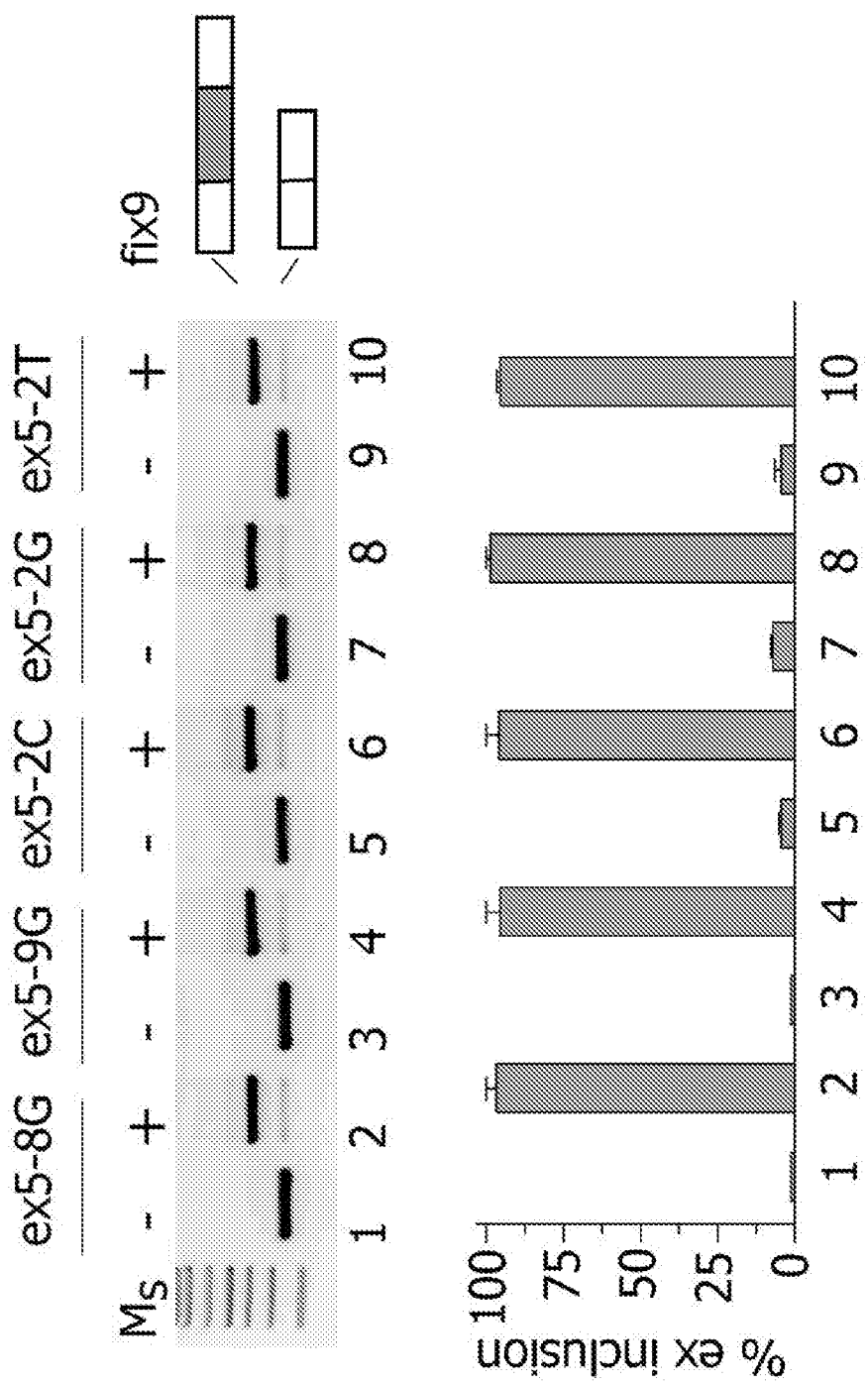
FIG. 7 illustrates results from Example 3, showing that one single modified U1snRNA, and particularly the one that pairs at position 9 (FIX9), is able to significantly restore splicing in the presence of all the different mutations investigated.

The data related to this finding, never reported till now, are shown in FIG. 7.

The effectiveness of any therapeutic approach is testified by the ability thereof to induce protein synthesis, the levels of which are decreased under the pathological conditions.

Figure 8:
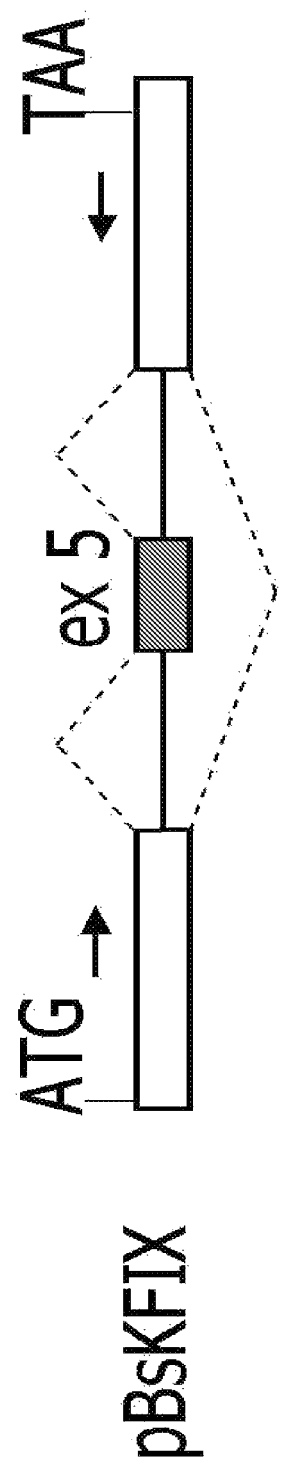
FIG. 8 illustrates a construct wherein a minigene was created in which exon 5 and its flanking intronic sequences have been inserted into the FIX full-length encoding sequence, and cloned into vector pBskFIX. The rectangles indicate the coding sequences, with the ATG start codon and the TAA stop codon, whereas the introns are shown as lines.

To verify if the correction observed at the messenger RNA level results in an increased synthesis and function of secreted FIX, a minigene was created in which exon 5 and its flanking intronic sequences have been inserted into the FIX full-length encoding sequence. FIG. 8 schematically reports the construct generated for this study and cloned into vector pBskFIX. The rectangles indicate the coding sequences, with the ATG start codon and the TAA stop codon, whereas the introns are reported as lines.

Figure 9:
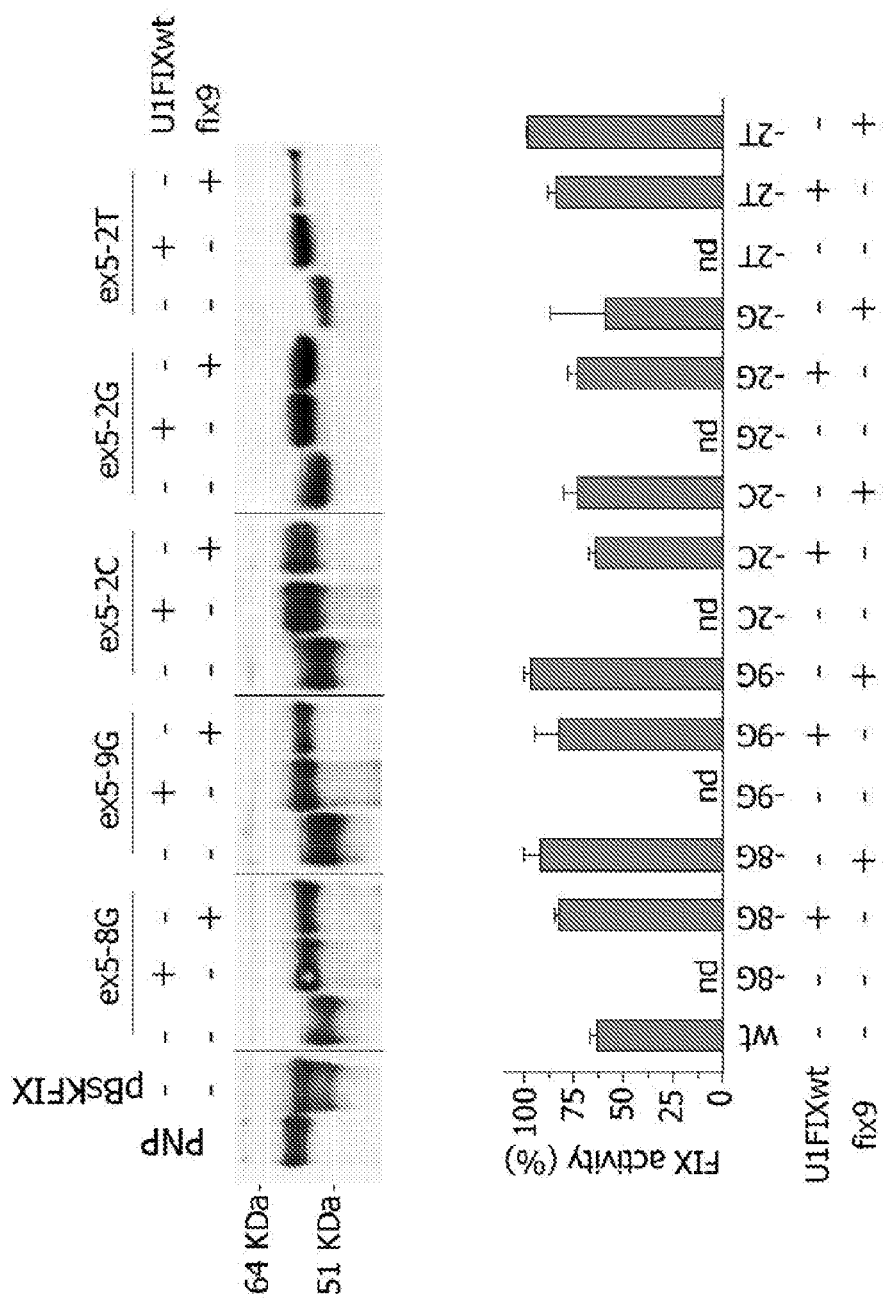
FIG. 9 illustrates the results of transfecting the minigene illustrated by FIG. 8 into BHK hamster kidney cells, selected for their ability to synthesize and secrete a functional FIX, demonstrating that the messenger RNA is correctly processed and translated into protein.

Transfection of this minigene into BHK hamster kidney cells, selected for their ability to synthesize and secrete a functional FIX, demonstrated that the messenger RNA is correctly processed and translated into protein (FIG. 9). In fact, considerable amounts of functional protein are measured in the culture medium. By contrast, mutations in the donor site (−2A>G, −2A>T) or in the acceptor site (−8T>G, −9T>G) cause exclusion of exon 5 and synthesis of a truncated protein variant not functional in a normal clotting assay. By Western blotting (upper panel), the mutation was actually proven to cause synthesis of a FIX variant having a lower molecular weight, due to the absence of exon 5 in the coding sequence. No appreciable clotting activity corresponds to this form (lower panel). Expression of the intronic ExSpeU1 fix9 is able to restore splicing and increase the levels of functional secreted FIX up to levels that, if reached in patients, would be largely above the therapeutic threshold. These results confirm the effectiveness of the ExSpeU1 approach.

Example 4: Spinal Muscular Atrophy

Figure 10:
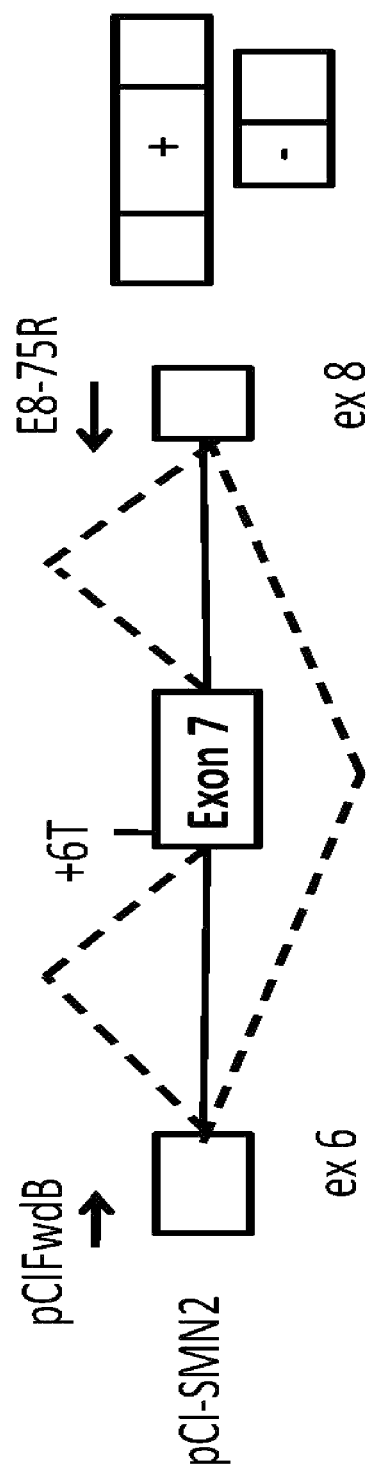
FIG. 10 schematically illustrates the pCI-SMN2 minigene.

Vectors expressing the SMN1 (pCI-SMN1) and SMN2 (pCI-SMN2) minigenes were used for the study (Hua et al., 2007). Such minigenes are widely used to validate the effect of therapeutic molecules capable of correcting the splicing defect in the SMN2 gene (Hua et al., 2007; Hua et al., 2008). The two minigenes are composed of 111 nucleotides of exon 6, 200 nucleotides of intron 6, the 54 nucleotides of exon 7, the 444 nucleotides of intron 7, and the first 75 nucleotides of exon 8, under the control of the CMV promoter. The two minigenes differ for the presence of one nucleotide substitution at position 6 in exon 7. In pCI-SMN1 there is a C, whereas in pCI-SMN2 there is a T. Such a synonymous substitution induces a splicing defect in pCI-SMN2 with skipping of exon 7 in the mature transcript. The pCI-SMN2 minigene is schematically represented in FIG. 10. The synonymous variant at position +6T in the exon, which induces exon skipping, is indicated.

Many experimental evidences have demonstrated that the correction of the splicing in the SMN2 gene represents an effective therapeutic strategy in SMA (Hua et al., 2007; Hua et al., 2008; Lorson et al., 2010). Table 5 shows a list of the generated modified U1-snRNAs, the target sequences thereof, and their localization around the donor site. The different modified U1-snRNAs and their effect on the percentage of exon 7 inclusion were tested in the SMN2 minigene.

TABLE 5

Recognition sequences (U1-SR) in the gene for the modified U1-snRNAs for the correction of the splicing defect of exon 7 in the SMN2 gene

| SMN U1-snRNAs | Binding sequence (5' → 3') | Target sequence (5' → 3') | Length (bp) |
|---|---|---|---|
| -1G-2G-3A | acuuacucc | ggagtaagt | 9 |
| SMN_SH 2 | gcagacuua | taagtctgc | 9 |
| SMN_SH 17 | acuuucaua | tatgaaagt | 9 |
| SMN_SH 25 | uacaaaaguaagauuca (SEQ ID NO: 83) | tgaatcttactttgta (SEQ ID NO: 85) | 17 |
| SMN_SH 37 | aaaccauaaaguuuuacaa (SEQ ID NO: 84) | ttgtaaaactttatggttt (SEQ ID NO: 86) | 19 |
| SMN_SH 40 | caaaccauaaaguuuua (SEQ ID NO: 96) | taaaactttatggtttg (SEQ ID NO: 103) | 17 |

Figure 11:
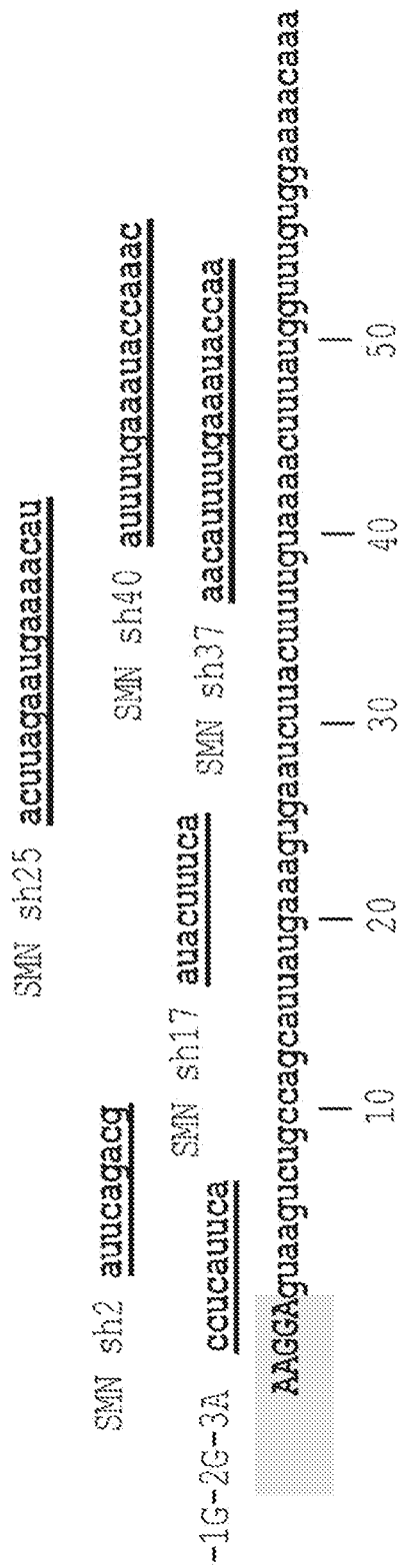
FIG. 11 illustrates the localization of the modified SMN U1 snRNAs employed for correcting the splicing defect of the SMN2 gene.

FIG. 11 shows the localization of the modified SMN U1 snRNAs employed for correcting the splicing defect of the SMN2 gene.

The minigenes were inserted into HeLa cells by transient transfection with Lipofectamine (liposomes). The RNA was analyzed by RT-PCR as indicated in Example 2. The RNA extracted from the cells was then subjected to RT-PCR with primers pCIFwdB and E8-75 R to assess the splicing products.

As can be observed in FIG. 12, transfection of the pCI SMN2 plasmid into cultured cells mainly shows skipping of exon 7 (lane 1). Co-transfection of the U1ex7SMN −1G-2G-3A (well 2), U1ex7SMN sh2 (well 3), U1ex7SMN sh17 (well 4), U1ex7SMN sh25 (well 5), U1ex7SMN sh37 (well 6) and U1ex7SMN sh40 (well 7) plasmids induces a significant increase in the percentage of inclusion of exon 7.

In particular, FIG. 12 shows the effect of the modified SMN U1s on SMN2 splicing. The splicing profile of exon 7 of the SMN2 gene (well 1) and the effect of co-expression of the modified U1 snRNAs (wells 2-7) are indicated in the upper part of the figure. The two exon 7 inclusion (+) and exclusion (−) isoforms are indicated. In the lower panel the histogram shows the percentage of inclusion of exon 7, and thus, of the correct splicing. The data are the average of three independent experiments.

Example 5: Mutations in the Exon and CFTR Exon 12 Donor Site Associated with Cystic Fibrosis Cystic fibrosis is caused by mutations in the CFTR gene. Mutations localized in exon 12 splicing site, associated with serious disease forms, which induce aberrant exon skipping are indicated in Table 6. A few mutations localized in exon 12 induce exon skipping (Pagani et al., 2003). Exonic mutations that induce exclusion of exon 12 are indicated in Table 7.

TABLE 6

List of mutations in exon 12 donor site of the CFTR gene. The mutations are shown in bold

| Position | Nucleotide substitution | Sequence of CF exon 12 donor site Positions: −3 −2 −1\ +1+2+3+4+5+6 |
|---|---|---|
| −1 | G > A | AAA\gtatgt |
| −1 | G > T | AAT\gtatgt |
| +3 | A > G | AAG\gtgtgt |
| +3 | A > C | AAG\gtcgt |
| +5 | T > A | AAG\gtatat |

TABLE 7

| Nucleotide substitution | Amino acid substitution | Position in the exon |
|---|---|---|
| G > A | A566T | +17 |
| C > T | Y577Y | +52 |

Table 8 shows the recognition sequence in the U1-snRNA gene modified for the correction of the splicing defects in exon 12 of the CFTR gene, which was selected from a larger panel of modified U1 snRNAs.

TABLE 8

| CFTR U1-snRNAs | Binding Sequence (5' → 3') | Target Sequence (5' → 3') | Length (bp) |
|---|---|---|---|
| cf11 | AUAAGUAAGGUAUUCA (SEQ ID NO: 4) | TGAATACCTTACTTAT (SEQ ID NO: 3) | 16 |

The pTB CFex12 minigene employed is schematically represented in FIG. 13 (Pagani et al., 2003). The rectangles represent the middle regions of the α-globin construct, and of the CFTR exon 12, with introns represented as lines. Exon 12 and the flanking intronic regions were cloned into plasmid pTB. The transcription is under the control of the α-globin promoter and SV40 enhancer. The two possible splicing isoforms are indicated.

FIG. 14 shows the localization of the ExSpeU1 cf1 1 that was used for correcting the splicing defects of exon 12 of the CFTR gene.

The RNA was analyzed by RT-PCR as indicated in Example 2: transfection of the minigenes into cultured cells and analysis of the splicing products, by using alfa2-3 and BRA2 as the primers and the minigene.

FIG. 15 shows the effect of ExSPeU1 cf1 1 on the aberrant splicing induced by different types of mutations localized in the 5'ss and in the exon. ExSPeU1 cf1 1 induces a significant increase in the percentage of inclusion of exon 12 in all the mutants analyzed.

The splicing profile of the different variants (odd wells) and the effect of co-expression of ExSPeU1 cf1 1 (even wells) are indicated in the upper part of FIG. 15. The two exon 12 inclusion (+) and exclusion (−) isoforms are indicated. In the lower panel the histogram shows the percentage of inclusion of exon 12, and thus, of the correct splicing. The data are the average of 3 independent experiments.

The cells were transfected with 0.5 μg of vectors expressing each specific variant. The splicing profile was assessed by RT-PCR with primers ALPHA2,3 and BRA2. The amplified fragments were separated on a 2% agarose gel. The identity of the transcripts including (+) or excluding (−) exon 12 is indicated on the right-hand side of the gel and has been validated by sequencing.

Example 6: Mutation in the IKBKAP Exon 20 Donor Splice Site Associated with Familial Dysautonomia The most frequent mutation associated with Familial Dysautonomia is the intronic point substitution IVS20+6 T>C, which affects the donor splice site of the IKBKAP exon 20 (Anderson et al. 2001; Slaugenhaupt 2001). This mutation reduces the affinity of the endogenous U1 snRNA, promoting the skipping of exon 20 (Carmel et al. 2004). The hybrid minigene system used to study the aberrant processing of IKBKAP pre-mRNA is the above described pTB-NdeI plasmid (FIG. 16). The expression cassette cloned in this vector has been the genomic region of the IKBKAP gene spanning intron 18 to intron 22 (pTB IKAP wt) (FIG. 16). The intronic point mutation IVS20+6T>C was subsequently inserted by site-directed mutagenesis to create the pTB IKAP+6T>C vector. The rectangles represent the middle regions of the α-globin construct, and of the IKBKAP exons, with introns represented as lines. The transcription is under the control of the α-globin promoter and SV40 enhancer. The normal and aberrant (exon-skipping) splicing pathways are indicated by dotted lines.

Table 9 shows the IKAP ExSpeU1s binding regions within the IKBKAP intron 20, which are schematically represented in FIG. 17.

TABLE 9

| IKBKAP U1-snRNAs | Binding Sequence (5' → 3') | Target Sequence (5' → 3') | Length (bp) |
|---|---|---|---|
| IK2 | uggcgcuua | taagcgcca | 9 |
| IK4 | aauggcgcu | agcgccatt | 9 |
| IK5 | aguacaauggcgc (SEQ ID NO: 87) | gcgccattgtact (SEQ ID NO: 91) | 13 |
| IK10L | gcaaacaguacaau (SEQ ID NO: 88) | attgtactgtttgc (SEQ ID NO: 92) | 14 |
| IK12 | ucgcaaacaguaca (SEQ ID NO: 89) | tgtactgtttgcga (SEQ ID NO: 93) | 14 |
| IK15 | gcaaacagu | actgtttgc | 9 |
| IK19 | cuagucgcaaac (SEQ ID NO: 90) | gtttgcgactag (SEQ ID NO: 94) | 12 |

FIG. 18 shows the effects of the different ExSpeU1s on the aberrant splicing induced by the mutation causing familial dysautonomia. The mutation promotes exon 20 skipping, as indicated by the intensity of the lower band (lane 2), which is not appreciable in the wild-type context (lane 1).

The splicing correction is appreciable from lane 3 to lane 9 in which the mutant minigene (+6 T/C) has been co-expressed together with the different IKBKAP ExSpeU1 variants. All the ExSpeU1s efficiently promoted the inclusion of exon 20.

Human neuronal SH-SY5Y cells were transfected with 0.5 μg of vectors expressing the wild-type and mutated IKBKAP minigenes. The splicing profile was assessed by RT-PCR with primer ALPHA2,3 and a reverse primer in exon 21 (Exon21 R) (FIG. 16). The amplified fragments were separated on a 2% agarose gel. The identity of the transcripts including or excluding exon 20 (see schematic representation on the right) has been validated by sequencing. In the lower panel of FIG. 18 the histograms report the % of exon 20 inclusion and the results are expressed as mean±standard deviation in at least three independent experiments.

INCORPORATION BY REFERENCE

Numerous references, and other documents, are cited throughout the application, the contents of which are hereby incorporated by reference herein, in their entireties.

REFERENCES

Anderson S L, Coli R, Daly I W, Kichula E A, Rork M J, Volpi S A, Ekstein J, Rubin B Y. 2001. Familial dysautonomia is caused by mutations of the IKAP gene. Am. J. Hum. Genet. 68, 753-758.

Carmel I, Tal S, Vig I, Ast G. 2004. Comparative analysis detects dependencies among the 59 splice-site positions. RNA 10: 828-840.

Cartegni, L., S. L. Chew, and A. R. Krainer. 2002. Listening to silence and understanding nonsense: exonic mutations that affect splicing. Nat Rev Genet 3:285-98.

Dal Mas A, Rogalska M E, Bussani E, Pagani F. Improvement of SMN2 pre-mRNA processing mediated by exon-specific U1 small nuclear RNA. Am J Hum Genet. 2015 Jan. 8; 96(1):93-103.

Fernandez Alanis, Pinotti M, Dal Mas A, Balestra D, Cavallari N, Rogalska M E, Bernardi F, Pagani F. An exon-specific U1 small nuclear RNA (snRNA) strategy to correct splicing defects. Hum Mol Genet. 2012 Jun. 1; 21(11):2389-98.

Horowitz D S, Krainer A R. Mechanisms for selecting 5' splice sites in mammalian pre-mRNA splicing. Trends Genet. 1994 March; 10(3):100-6.

Hua, Y., T. A. Vickers, B. F. Baker, C. F. Bennett, and A. R. Krainer. 2007. Enhancement of SMN2 exon 7 inclusion by antisense oligonucleotides targeting the exon. PLoS Biol 5:e73.

Hua, Y., T. A. Vickers, H. L. Okunola, C. F. Bennett, and A. R. Krainer. 2008. Antisense masking of an hnRNP A1/A2 intronic splicing silencer corrects SMN2 splicing in transgenic mice. Am J Hum Genet 82:834-48.

Lorson, C. L., H. Rindt, and M. Shababi. Spinal muscular atrophy: mechanisms and therapeutic strategies. Hum Mol Genet 19:R111-8.

Pagani, F., E. Buratti, C. Stuani, M. Romano, E. Zuccato, M. Niksic, L. Giglio, D. Faraguna, and F. E. Baralle. 2000. Splicing factors induce cystic fibrosis transmembrane regulator exon 9 skipping through a nonevolutionary conserved intronic element. J Biol Chem 275:21041-7.

Pagani, F., E. Buratti, C. Stuani, R. Bendix, T. Dork, and F. E. Baralle. 2002. A new type of mutation causes a splicing defect in ATM. Nat Genet 30:426-9.

Pagani, F., C. Stuani, M. Tzetis, E. Kanavakis, A. Efthymiadou, S. Doudounakis, T. Casals, and F. E. Baralle. 2003. New type of disease causing mutations: the example of the composite exonic regulatory elements of splicing in CFTR exon 12. Hum Mol Genet 12:1111-20.

Pagani, F., and F. E. Baralle. 2004. Genomic variants in exons and introns: identifying the splicing spoilers. Nat Rev Genet 5:389-96.

Pinotti, M., L. Rizzotto, D. Balestra, M. A. Lewandowska, N. Cavallari, G. Marchetti, F. Bernardi and F. Paganil. Maestri, F. Pagani, and F. Bernardi. 2008. U1-snRNA mediated rescue of mRNA processing in severe factor VII deficiency. Blood 111:2681-2684

Pinotti, M., D. Balestra, L. Rizzotto, I. Maestri, F. Pagani, and F. Bernardi. 2009. Rescue of coagulation factor VII function by the U1+5A snRNA. Blood 113:6461:6464.

Slaugenhaupt S A, Blumenfeld A, Gill S P, Leyne M, Mull J, Cuajungco M P, Liebert C B, Chadwick B, Idelson M, Reznik L, Robbins C, Makalowska I, Brownstein M, Krappmann D, Scheidereit C, Maayan C, Axelrod F B, Gusella J F. 2001. Tissue-specific expression of a splicing mutation in the IKBKAP gene causes familial dysautonomia. Am. J. Hum. Genet. 68, 598-605.

```
SEQUENCE LISTING

<160> NUMBER OF SEQ ID NOS: 104

<210> SEQ ID NO 1
<211> LENGTH: 10
<212> TYPE: RNA
<213> ORGANISM: artificial sequence
<220> FEATURE:
<223> OTHER INFORMATION: FIX1, binding sequence of the modified
      U1-snRNAs for the correction of the splicing defects of exon 5
      of the factor IX gene

<400> SEQUENCE: 1
agauuaugac                                                          10

<210> SEQ ID NO 2
<211> LENGTH: 11
<212> TYPE: RNA
<213> ORGANISM: artificial sequence
<220> FEATURE:
<223> OTHER INFORMATION: FIX7, binding sequence of the modified
      U1-snRNAs for the correction of the splicing defects of exon 5
      of the factor IX gene

<400> SEQUENCE: 2
ucuuauucag a                                                        11

<210> SEQ ID NO 3
<211> LENGTH: 16
<212> TYPE: DNA
<213> ORGANISM: Homo sapiens

<400> SEQUENCE: 3 tgaataccctt acttat                                                  16

<210> SEQ ID NO 4
<211> LENGTH: 16
<212> TYPE: RNA
<213> ORGANISM: artificial sequence
<220> FEATURE:
<223> OTHER INFORMATION: Binding sequence, in the U1-snRNA gene modified
      for the correction of the splicing defects in exon 12 of the CFTR
```

```
    gene

<400> SEQUENCE: 4
auaaguaagg uauuca                                                        16

<210> SEQ ID NO 5
<211> LENGTH: 592
<212> TYPE: DNA
<213> ORGANISM: Homo sapiens

<400> SEQUENCE: 5
taaggaccag cttctttggg agagaacaga cgcaggggcg ggagggaaaa agggagaggc         60
agacgtcact tccccttggc ggctctggca gcagattggt cggttgagtg gcagaaaggc        120
agacggggac tgggcaaggc actgtcggtg acatcacgga cagggcgact tctatgtaga        180
tgaggcagcg cagaggctga cgtcttcgcc acttgctgct tcaccacgaa ggagttcccg        240
tgccctggga gcgggttcag gaccgctgat cggaagtgag aatcccagct gtgtgtcagg        300
gctggaaagg gctcggagt gcgcgggca agtgaccgtg tgtgtaaaga gtgaggcgta         360
tgaggctgtg tcggggcaga ggcccaagat ctgatactta cctggcaggg gagataccat        420
gatcacgaag gtggttttcc cagggcgagg cttatccatt gcactccgga tgtgctgacc        480
cctgcgattt ccccaaatgt gggaaactcg actgcataat tgtggtagt gggggactgc         540 gttcgcgctt tccctgact ttctggagtt caaaagtag actgtacgct aa                  592

<210> SEQ ID NO 6
<211> LENGTH: 33
<212> TYPE: DNA
<213> ORGANISM: artificial sequence
<220> FEATURE:
<223> OTHER INFORMATION: FIX U1ex5 C3T5A6 dir, for U1 FIX exon 5

<400> SEQUENCE: 6
gatctcatta tgacctggca ggggagatac cat                                     33

<210> SEQ ID NO 7
<211> LENGTH: 33
<212> TYPE: DNA
<213> ORGANISM: artificial sequence
<220> FEATURE:
<223> OTHER INFORMATION: FIX U ex5 C3T5A6 rev, for U1 FIX exon 5

<400> SEQUENCE: 7
gatcatggta tctcccctgc caggtcataa tga                                     33

<210> SEQ ID NO 8
<211> LENGTH: 36
<212> TYPE: DNA
<213> ORGANISM: artificial sequence
<220> FEATURE:
<223> OTHER INFORMATION: U1FIXex5 SH-7 dir, for U1 FIX exon 5

<400> SEQUENCE: 8
gatctcatat gacctgctgg gcaggggaga taccat                                  36

<210> SEQ ID NO 9
<211> LENGTH: 36
<212> TYPE: DNA
<213> ORGANISM: artificial sequence
<220> FEATURE:
<223> OTHER INFORMATION: U1FIXex5 SH-7 rev, for U1 FIX exon 5

<400> SEQUENCE: 9
```

```
gatcatggta tctcccctgc ccagcaggtc atatga                         36

<210> SEQ ID NO 10
<211> LENGTH: 34
<212> TYPE: DNA
<213> ORGANISM: artificial sequence
<220> FEATURE:
<223> OTHER INFORMATION: U1FIXex5 SH1 dir, for U1 FIX exon 5

<400> SEQUENCE: 10
gatctcatag attatgacgc agggagata ccat                            34

<210> SEQ ID NO 11
<211> LENGTH: 34
<212> TYPE: DNA
<213> ORGANISM: artificial sequence
<220> FEATURE:
<223> OTHER INFORMATION: U1FIXex5 SH1 rev, for U1 FIX exon 5

<400> SEQUENCE: 11
gatcatggta tctcccctgc gtcataatct atga                           34

<210> SEQ ID NO 12
<211> LENGTH: 35
<212> TYPE: DNA
<213> ORGANISM: artificial sequence
<220> FEATURE:
<223> OTHER INFORMATION: U1FIXex5 SH7 rev, for U1 FIX exon 5

<400> SEQUENCE: 12
gatctcatct tattcagatg caggggagat accat                          35

<210> SEQ ID NO 13
<211> LENGTH: 35
<212> TYPE: DNA
<213> ORGANISM: artificial sequence
<220> FEATURE:
<223> OTHER INFORMATION: U1FIXex5 SH7 rev, for U1 FIX exon 5

<400> SEQUENCE: 13
gatcatggta tctcccctgc atctgaataa gatga                          35

<210> SEQ ID NO 14
<211> LENGTH: 34
<212> TYPE: DNA
<213> ORGANISM: artificial sequence
<220> FEATURE:
<223> OTHER INFORMATION: U1FIXex5 SH9 dir, for U1 FIX exon 5

<400> SEQUENCE: 14
gatctcattc ttattcaggc agggagata ccat                            34

<210> SEQ ID NO 15
<211> LENGTH: 34
<212> TYPE: DNA
<213> ORGANISM: artificial sequence
<220> FEATURE:
<223> OTHER INFORMATION: U1FIXex5 SH9 rev, for U1 FIX exon 5

<400> SEQUENCE: 15
gatcatggta tctcccctgc ctgaataaga atga                           34

<210> SEQ ID NO 16
<211> LENGTH: 34
<212> TYPE: DNA
```

```
<213> ORGANISM: artificial sequence
<220> FEATURE:
<223> OTHER INFORMATION: U1FIXex5 SH10 dir, for U1 FIX exon 5

<400> SEQUENCE: 16
gatctcatat cttattcagc agggagata ccat                             34

<210> SEQ ID NO 17
<211> LENGTH: 34
<212> TYPE: DNA
<213> ORGANISM: artificial sequence
<220> FEATURE:
<223> OTHER INFORMATION: U1FIXex5 SH10 rev, for U1 FIX exon 5

<400> SEQUENCE: 17
gatcatggta tctcccctgc tgaataagat atga                            34

<210> SEQ ID NO 18
<211> LENGTH: 34
<212> TYPE: DNA
<213> ORGANISM: artificial sequence
<220> FEATURE:
<223> OTHER INFORMATION: U1FIXex5 SH13 dir, for U1 FIX exon 5

<400> SEQUENCE: 18
gatctcataa aatcttatgc agggagata ccat                             34

<210> SEQ ID NO 19
<211> LENGTH: 34
<212> TYPE: DNA
<213> ORGANISM: artificial sequence
<220> FEATURE:
<223> OTHER INFORMATION: U1FIXex5 SH13 rev, for U1 FIX exon 5

<400> SEQUENCE: 19
gatcatggta tctcccctgc ataagatttt atga                            34

<210> SEQ ID NO 20
<211> LENGTH: 35
<212> TYPE: DNA
<213> ORGANISM: artificial sequence
<220> FEATURE:
<223> OTHER INFORMATION: U1FIXex5 SH16 dir, for U1 FIX exon 5

<400> SEQUENCE: 20
gatctcatat aaaaaatctg caggggagat accat                           35

<210> SEQ ID NO 21
<211> LENGTH: 35
<212> TYPE: DNA
<213> ORGANISM: artificial sequence
<220> FEATURE:
<223> OTHER INFORMATION: U1FIXex5 SH16 rev, for U1 FIX exon 5

<400> SEQUENCE: 21
gatcatggta tctcccctgc agatttttta tatga                           35

<210> SEQ ID NO 22
<211> LENGTH: 35
<212> TYPE: DNA
<213> ORGANISM: artificial sequence
<220> FEATURE:
<223> OTHER INFORMATION: U1FIXex5 SH22 dir, for U1 FIX exon 5

<400> SEQUENCE: 22
gatctcatat ttctttaaag caggggagat accat                           35
```

<210> SEQ ID NO 23
<211> LENGTH: 35
<212> TYPE: DNA
<213> ORGANISM: artificial sequence
<220> FEATURE:
<223> OTHER INFORMATION: U1FIXex5 SH22 rev, for U1 FIX exon 5

<400> SEQUENCE: 23
gatcatggta tctcccctgc tttaaagaaa tatga                               35

<210> SEQ ID NO 24
<211> LENGTH: 35
<212> TYPE: DNA
<213> ORGANISM: artificial sequence
<220> FEATURE:
<223> OTHER INFORMATION: U1FIXex5 SH33 dir, for U1 FIX exon 5

<400> SEQUENCE: 24
gatctcattc agatacagag caggggagat accat                               35

<210> SEQ ID NO 25
<211> LENGTH: 35
<212> TYPE: DNA
<213> ORGANISM: artificial sequence
<220> FEATURE:
<223> OTHER INFORMATION: U1FIXex5 SH33 rev, for U1 FIX exon 5

<400> SEQUENCE: 25
gatcatggta tctcccctgc tctgtatctg aatga                               35

<210> SEQ ID NO 26
<211> LENGTH: 34
<212> TYPE: DNA
<213> ORGANISM: artificial sequence
<220> FEATURE:
<223> OTHER INFORMATION: U1FIXex5 SH38 dir, for U1 FIX exon 5

<400> SEQUENCE: 26
gatctcatag tttcagatgc agggagata ccat                                 34

<210> SEQ ID NO 27
<211> LENGTH: 34
<212> TYPE: DNA
<213> ORGANISM: artificial sequence
<220> FEATURE:
<223> OTHER INFORMATION: U1FIXex5 SH38 rev, for U1 FIX exon 5

<400> SEQUENCE: 27
gatcatggta tctcccctgc atctgaaact atga                                34

<210> SEQ ID NO 28
<211> LENGTH: 34
<212> TYPE: DNA
<213> ORGANISM: artificial sequence
<220> FEATURE:
<223> OTHER INFORMATION: U1FIXex5 SH63 dir, for U1 FIX exon 5

<400> SEQUENCE: 28
gatctcattt atgtaggtgc agggagata ccat                                 34

<210> SEQ ID NO 29
<211> LENGTH: 34
<212> TYPE: DNA
<213> ORGANISM: artificial sequence
<220> FEATURE:

```
<223> OTHER INFORMATION: U1FIXex5 SH63 rev, for U1 FIX exon 5

<400> SEQUENCE: 29
gatcatggta tctcccctgc acctacataa atga                                34

<210> SEQ ID NO 30
<211> LENGTH: 34
<212> TYPE: DNA
<213> ORGANISM: artificial sequence
<220> FEATURE:
<223> OTHER INFORMATION: U1ex7SMN -1G-2G-3A rev, oligonucleotide for U1
      SMN

<400> SEQUENCE: 30
gatcatggta tctcccctgc ggagtaagtt atga                                34

<210> SEQ ID NO 31
<211> LENGTH: 34
<212> TYPE: DNA
<213> ORGANISM: artificial sequence
<220> FEATURE:
<223> OTHER INFORMATION: U1ex7SMN -1G-2G-3A dir, oligonucleotide for U1
      SMN.

<400> SEQUENCE: 31
gatctcataa cttactccgc aggggagata ccat                                34

<210> SEQ ID NO 32
<211> LENGTH: 34
<212> TYPE: DNA
<213> ORGANISM: artificial sequence
<220> FEATURE:
<223> OTHER INFORMATION: U1ex7SMN sh2 rev, oligonucleotide for U1 SMN.

<400> SEQUENCE: 32
gatcatggta tctcccctgc taagtctgct atga                                34

<210> SEQ ID NO 33
<211> LENGTH: 34
<212> TYPE: DNA
<213> ORGANISM: artificial sequence
<220> FEATURE:
<223> OTHER INFORMATION: U1ex7SMN sh2 dir, oligonucleotide for U1 SMN.

<400> SEQUENCE: 33
gatctcatag cagacttagc aggggagata ccat                                34

<210> SEQ ID NO 34
<211> LENGTH: 34
<212> TYPE: DNA
<213> ORGANISM: artificial sequence
<220> FEATURE:
<223> OTHER INFORMATION: U1ex7SMN sh17 rev, oligonucleotide for U1 SMN

<400> SEQUENCE: 34
gatcatggta tctcccctgc tatgaaagtt atga                                34

<210> SEQ ID NO 35
<211> LENGTH: 34
<212> TYPE: DNA
<213> ORGANISM: artificial sequence
<220> FEATURE:
<223> OTHER INFORMATION: U1ex7SMN sh17 dir, oligonucleotide for U1 SMN

<400> SEQUENCE: 35
gatctcataa ctttcatagc aggggagata ccat                                34
```

```
<210> SEQ ID NO 36
<211> LENGTH: 33
<212> TYPE: DNA
<213> ORGANISM: artificial sequence
<220> FEATURE:
<223> OTHER INFORMATION: U1-1A4T dir, oligonucleotide for U1 CFTR exon
      12

<400> SEQUENCE: 36
gatctcatac atacttggca ggggagatac cat                                33

<210> SEQ ID NO 37
<211> LENGTH: 33
<212> TYPE: DNA
<213> ORGANISM: artificial sequence
<220> FEATURE:
<223> OTHER INFORMATION: U1-1A4T rev, oligonucleotide for U1 CFTR exon
      12

<400> SEQUENCE: 37
gatcatggta tctcccctgc caagtatgta tga                                33

<210> SEQ ID NO 38
<211> LENGTH: 33
<212> TYPE: DNA
<213> ORGANISM: artificial sequence
<220> FEATURE:
<223> OTHER INFORMATION: U1G3T4 dir, oligonucleotide for U1 CFTR exon 12

<400> SEQUENCE: 38
gatctcatac acacctggca ggggagatac cat                                33

<210> SEQ ID NO 39
<211> LENGTH: 33
<212> TYPE: DNA
<213> ORGANISM: artificial sequence
<220> FEATURE:
<223> OTHER INFORMATION: U1G3T4 Rev, oligonucleotide for U1 CFTR exon 12

<400> SEQUENCE: 39
gatcatggta tctcccctgc caggtgtgta tga                                33

<210> SEQ ID NO 40
<211> LENGTH: 33
<212> TYPE: DNA
<213> ORGANISM: artificial sequence
<220> FEATURE:
<223> OTHER INFORMATION: U1 T4 A5 dir, oligonucleotide for U1 CFTR exon
      12

<400> SEQUENCE: 40
gatctcatat atacctggca ggggagatac cat                                33

<210> SEQ ID NO 41
<211> LENGTH: 33
<212> TYPE: DNA
<213> ORGANISM: artificial sequence
<220> FEATURE:
<223> OTHER INFORMATION: U1T4 A5 Rev, oligonucleotide for U1 CFTR exon
      12

<400> SEQUENCE: 41
gatcatggta tctcccctgc caggtatata tga                                33

<210> SEQ ID NO 42
```

```
<211> LENGTH: 35
<212> TYPE: DNA
<213> ORGANISM: artificial sequence
<220> FEATURE:
<223> OTHER INFORMATION: U1CFsh+1 dir, oligonucleotide for U1 CFTR exon
      12

<400> SEQUENCE: 42
gatctctcaa agaacatacg caggggagat accat                                  35

<210> SEQ ID NO 43
<211> LENGTH: 35
<212> TYPE: DNA
<213> ORGANISM: artificial sequence
<220> FEATURE:
<223> OTHER INFORMATION: U1CF sh+1 REV, oligonucleotide for U1 CFTR exon
      12

<400> SEQUENCE: 43
gatcatggta tctcccctgc gtatgttctt tgaga                                  35

<210> SEQ ID NO 44
<211> LENGTH: 35
<212> TYPE: DNA
<213> ORGANISM: artificial sequence
<220> FEATURE:
<223> OTHER INFORMATION: CF12 SH+9 Dir, oligonucleotide for U1 CFTR exon
      12

<400> SEQUENCE: 44
gatctcatag gtattcaaag caggggagat accat                                  35

<210> SEQ ID NO 45
<211> LENGTH: 35
<212> TYPE: DNA
<213> ORGANISM: artificial sequence
<220> FEATURE:
<223> OTHER INFORMATION: CF12 SH+9 Rev, oligonucleotide for U1 CFTR exon
      12

<400> SEQUENCE: 45
gatcatggta tctcccctgc tttgaatacc tatga                                  35

<210> SEQ ID NO 46
<211> LENGTH: 38
<212> TYPE: DNA
<213> ORGANISM: artificial sequence
<220> FEATURE:
<223> OTHER INFORMATION: CF12 SH+11 Dir, oligonucleotide for U1 CFTR
      exon 12

<400> SEQUENCE: 46
gatctcataa gtaaggtatt cagcagggga gataccat                               38

<210> SEQ ID NO 47
<211> LENGTH: 38
<212> TYPE: DNA
<213> ORGANISM: artificial sequence
<220> FEATURE:
<223> OTHER INFORMATION: CF12 SH+11 Rev, oligonucleotide for U1 CFTR
      exon 12

<400> SEQUENCE: 47
gatcatggta tctcccctgc tgaatacctt acttatga                               38

<210> SEQ ID NO 48
<211> LENGTH: 35
```

```
<212> TYPE: DNA
<213> ORGANISM: artificial sequence
<220> FEATURE:
<223> OTHER INFORMATION: CF12 SH+33 Dir, oligonucleotide for U1 CFTR
      exon 12

<400> SEQUENCE: 48
gatcatggta tctcccctgc tcatgctaaa ataga                            35

<210> SEQ ID NO 49
<211> LENGTH: 35
<212> TYPE: DNA
<213> ORGANISM: artificial sequence
<220> FEATURE:
<223> OTHER INFORMATION: CF12 SH+33 Rev, oligonucleotide for U1 CFTR
      exon 12

<400> SEQUENCE: 49
gatctctatt ttagcatgag cagggagat accat                             35

<210> SEQ ID NO 50
<211> LENGTH: 11
<212> TYPE: RNA
<213> ORGANISM: artificial sequence
<220> FEATURE:
<223> OTHER INFORMATION: FIX-7, binding sequence of the modified U1-
      snRNAs for the correction of the splicing defects of exon 5 of
      the factor IX gene

<400> SEQUENCE: 50
ugaccugcug g                                                      11

<210> SEQ ID NO 51
<211> LENGTH: 12
<212> TYPE: RNA
<213> ORGANISM: artificial sequence
<220> FEATURE:
<223> OTHER INFORMATION: Capable of recognizing the splicing donor site.

<400> SEQUENCE: 51
auacuuaccu gg                                                     12

<210> SEQ ID NO 52
<211> LENGTH: 15
<212> TYPE: DNA
<213> ORGANISM: artificial sequence
<220> FEATURE:
<223> OTHER INFORMATION: Oligonucleotide specific for generating
      modified UlsnRNAs when used to replace sequences encoding the
      U1snRNA single stranded tail region.
<220> FEATURE:
<221> NAME/KEY: misc_feature
<222> LOCATION: (3)..(4)
<223> OTHER INFORMATION: k is g or t

<400> SEQUENCE: 52
tgckkctttt agatg                                                  15

<210> SEQ ID NO 53
<211> LENGTH: 13
<212> TYPE: DNA
<213> ORGANISM: artificial sequence
<220> FEATURE:
<223> OTHER INFORMATION: Oligonucleotide specific for generating
      modified UlsnRNAswhen used to replace sequences encoding the
      U1snRNA single stranded tail region.
<220> FEATURE:
<221> NAME/KEY: misc_feature
<222> LOCATION: (2)..(2)
```

```
<223> OTHER INFORMATION: n is a, c, g, or t

<400> SEQUENCE: 53
cnggtcataa tct                                                              13

<210> SEQ ID NO 54
<211> LENGTH: 77
<212> TYPE: DNA
<213> ORGANISM: artificial sequence
<220> FEATURE:
<223> OTHER INFORMATION: Modified U1snRNA employed for the correction
      of exon 5 splicing defects of the clotting factor IX gene.

<400> SEQUENCE: 54
ccagcaggtc ataatctgaa taagatttttt taaagaaaat ctgtatctga aacttcagca          60
ttttaacaaa cctacat                                                          77

<210> SEQ ID NO 55
<211> LENGTH: 47
<212> TYPE: DNA
<213> ORGANISM: Homo sapiens

<400> SEQUENCE: 55
aaaggtatgt tctttgaata ccttacttat aatgctcatg ctaaaat                         47

<210> SEQ ID NO 56
<211> LENGTH: 15
<212> TYPE: DNA
<213> ORGANISM: artificial sequence
<220> FEATURE:
<223> OTHER INFORMATION: Sequence of acceptor/donor site

<400> SEQUENCE: 56
tgctgctttt agatg                                                            15

<210> SEQ ID NO 57
<211> LENGTH: 15
<212> TYPE: DNA
<213> ORGANISM: artificial sequence
<220> FEATURE:
<223> OTHER INFORMATION: Sequence of acceptor/donor site

<400> SEQUENCE: 57
tgcgtctttt agatg                                                            15

<210> SEQ ID NO 58
<211> LENGTH: 13
<212> TYPE: RNA
<213> ORGANISM: artificial sequence
<220> FEATURE:
<223> OTHER INFORMATION: FIX33 Binding Sequence

<400> SEQUENCE: 58
auucagauac aga                                                              13

<210> SEQ ID NO 59
<211> LENGTH: 12
<212> TYPE: RNA
<213> ORGANISM: artificial sequence
<220> FEATURE:
<223> OTHER INFORMATION: FIX38 Binding Sequence

<400> SEQUENCE: 59
auaguuucag au                                                               12
```

<210> SEQ ID NO 60
<211> LENGTH: 12
<212> TYPE: RNA
<213> ORGANISM: artificial sequence
<220> FEATURE:
<223> OTHER INFORMATION: FIX63 Binding Sequence

<400> SEQUENCE: 60
auuuauguag gu                                                            12

<210> SEQ ID NO 61
<211> LENGTH: 34
<212> TYPE: DNA
<213> ORGANISM: artificial sequence
<220> FEATURE:
<223> OTHER INFORMATION: Oligonucleotide specific for generating
      modified U1 IKBKAP sh2 dir.

<400> SEQUENCE: 61
gatctcatat ggcgcttagc aggggagata ccat                                    34

<210> SEQ ID NO 62
<211> LENGTH: 34
<212> TYPE: DNA
<213> ORGANISM: artificial sequence
<220> FEATURE:
<223> OTHER INFORMATION: Oligonucleotide specific for generating
      modified U1 IKBKAP sh2 rev.

<400> SEQUENCE: 62
gatcatggta tctcccctgc taagcgccat atga                                    34

<210> SEQ ID NO 63
<211> LENGTH: 34
<212> TYPE: DNA
<213> ORGANISM: artificial sequence
<220> FEATURE:
<223> OTHER INFORMATION: Oligonucleotide specific for generating
      modified U1 IKBKAP sh4 dir.

<400> SEQUENCE: 63
gatctcataa atggcgctgc aggggagata ccat                                    34

<210> SEQ ID NO 64
<211> LENGTH: 34
<212> TYPE: DNA
<213> ORGANISM: artificial sequence
<220> FEATURE:
<223> OTHER INFORMATION: Oligonucleotide specific for generating
      modified U1 IKBKAP sh4 rev.

<400> SEQUENCE: 64
gatcatggta tctcccctgc agcgccattt atga                                    34

<210> SEQ ID NO 65
<211> LENGTH: 38
<212> TYPE: DNA
<213> ORGANISM: artificial sequence
<220> FEATURE:
<223> OTHER INFORMATION: Oligonucleotide specific for generating
      modified U1 IKBKAP sh5 dir

<400> SEQUENCE: 65
gatctcataa gtacaatggc gcgcagggga gataccat                                38

<210> SEQ ID NO 66

-continued

```
<211> LENGTH: 38
<212> TYPE: DNA
<213> ORGANISM: artificial sequence
<220> FEATURE:
<223> OTHER INFORMATION: Oligonucleotide specific for generating
      modified U1 IKBKAP sh5 rev

<400> SEQUENCE: 66
gatcatggta tctcccctgc gcgccattgt acttatga                              38

<210> SEQ ID NO 67
<211> LENGTH: 39
<212> TYPE: DNA
<213> ORGANISM: artificial sequence
<220> FEATURE:
<223> OTHER INFORMATION: Oligonucleotide specific for generating
      modified U1 IKBKAP sh10L dir

<400> SEQUENCE: 67
gatctcatag caaacagtac aatgcagggg agataccat                             39

<210> SEQ ID NO 68
<211> LENGTH: 39
<212> TYPE: DNA
<213> ORGANISM: artificial sequence
<220> FEATURE:
<223> OTHER INFORMATION: Oligonucleotide specific for generating
      modified U1 IKBKAP sh10L rev

<400> SEQUENCE: 68
gatcatggta tctcccctgc attgtactgt ttgctatga                             39

<210> SEQ ID NO 69
<211> LENGTH: 39
<212> TYPE: DNA
<213> ORGANISM: Artificial Sequence
<220> FEATURE:
<223> OTHER INFORMATION: Oligonucleotide specific for generating
      modified U1 IKBKAP sh12 dir

<400> SEQUENCE: 69
gatctcatat cgcaaacagt acagcagggg agataccat                             39

<210> SEQ ID NO 70
<211> LENGTH: 39
<212> TYPE: DNA
<213> ORGANISM: artificial sequence
<220> FEATURE:
<223> OTHER INFORMATION: Oligonucleotide specific for generating
      modified U1 IKBKAP sh12 rev

<400> SEQUENCE: 70
gatcatggta tctcccctgc tgtactgttt gcgatatga                             39

<210> SEQ ID NO 71
<211> LENGTH: 34
<212> TYPE: DNA
<213> ORGANISM: artificial sequence
<220> FEATURE:
<223> OTHER INFORMATION: Oligonucleotide specific for generating
      modified U1 IKBKAP sh15 dir

<400> SEQUENCE: 71
gatctcatag caaacagtgc agggagata ccat                                   34

<210> SEQ ID NO 72
<211> LENGTH: 34
```

```
<212> TYPE: DNA
<213> ORGANISM: artificial sequence
<220> FEATURE:
<223> OTHER INFORMATION: Oligonucleotide specific for generating
      modified U1 IKBKAP sh15 rev

<400> SEQUENCE: 72
gatcatggta tctcccctgc actgtttgct atga                               34

<210> SEQ ID NO 73
<211> LENGTH: 37
<212> TYPE: DNA
<213> ORGANISM: artificial sequence
<220> FEATURE:
<223> OTHER INFORMATION: Oligonucleotide specific for generating
      modified U1 IKBKAP sh19 dir

<400> SEQUENCE: 73
gatctcatac tagtcgcaaa cgcaggggag ataccat                            37

<210> SEQ ID NO 74
<211> LENGTH: 37
<212> TYPE: DNA
<213> ORGANISM: artificial sequence
<220> FEATURE:
<223> OTHER INFORMATION: Oligonucleotide specific for generating
      modified U1 IKBKAP sh19 rev

<400> SEQUENCE: 74
gatcatggta tctcccctgc gtttgcgact agtatga                            37

<210> SEQ ID NO 75
<211> LENGTH: 34
<212> TYPE: DNA
<213> ORGANISM: artificial sequence
<220> FEATURE:
<223> OTHER INFORMATION: Oligonucleotide specific for generating
      modified U1 IKBKAP sh33 dir

<400> SEQUENCE: 75
gatctcataa tcacaagcgc aggggagata ccat                               34

<210> SEQ ID NO 76
<211> LENGTH: 34
<212> TYPE: DNA
<213> ORGANISM: artificial sequence
<220> FEATURE:
<223> OTHER INFORMATION: Oligonucleotide specific for generating
      modified U1 IKBKAP sh33 rev

<400> SEQUENCE: 76
gatcatggta tctcccctgc gcttgtgatt atga                               34

<210> SEQ ID NO 77
<211> LENGTH: 11
<212> TYPE: DNA
<213> ORGANISM: Homo sapiens

<400> SEQUENCE: 77
ccagcaggtc a                                                        11

<210> SEQ ID NO 78
<211> LENGTH: 10
<212> TYPE: DNA
<213> ORGANISM: Homo sapiens

<400> SEQUENCE: 78
```

-continued

```
gtcataatct                                                              10

<210> SEQ ID NO 79
<211> LENGTH: 11
<212> TYPE: DNA
<213> ORGANISM: Homo sapiens

<400> SEQUENCE: 79
tctgaataag a                                                            11

<210> SEQ ID NO 80
<211> LENGTH: 13
<212> TYPE: DNA
<213> ORGANISM: Homo sapiens

<400> SEQUENCE: 80
tctgtatctg aat                                                          13

<210> SEQ ID NO 81
<211> LENGTH: 12
<212> TYPE: DNA
<213> ORGANISM: Homo sapiens

<400> SEQUENCE: 81
atctgaaact at                                                           12

<210> SEQ ID NO 82
<211> LENGTH: 12
<212> TYPE: DNA
<213> ORGANISM: Homo sapiens

<400> SEQUENCE: 82
acctacataa at                                                           12

<210> SEQ ID NO 83
<211> LENGTH: 17
<212> TYPE: RNA
<213> ORGANISM: artificial sequence
<220> FEATURE:
<223> OTHER INFORMATION: SMN_SH 25, binding sequence (U1-SR) in the
      gene for the modified U1-snRNAs for the correction of the splicing
      defect of exon 7 in the SMN2 gene

<400> SEQUENCE: 83
uacaaaagua agauuca                                                      17

<210> SEQ ID NO 84
<211> LENGTH: 19
<212> TYPE: RNA
<213> ORGANISM: artificial sequence
<220> FEATURE:
<223> OTHER INFORMATION: SMN_SH 37, binding sequence, recognition
      sequence (U1-SR) in the gene for the modified U1-snRNAs for the
      correction of the splicing defect of exon 7 in the SMN2 gene.

<400> SEQUENCE: 84
aaaccauaaa guuuuacaa                                                    19

<210> SEQ ID NO 85
<211> LENGTH: 17
<212> TYPE: DNA
<213> ORGANISM: Homo sapiens

<400> SEQUENCE: 85
```

```
tgaatcttac ttttgta                                                      17

<210> SEQ ID NO 86
<211> LENGTH: 19
<212> TYPE: DNA
<213> ORGANISM: Homo sapiens

<400> SEQUENCE: 86
ttgtaaaact ttatggttt                                                    19

<210> SEQ ID NO 87
<211> LENGTH: 13
<212> TYPE: RNA
<213> ORGANISM: artificial sequence
<220> FEATURE:
<223> OTHER INFORMATION: IK5, IKAP ExSpeU1s binding region within the
      IKBKAP intron 20 binding sequence.

<400> SEQUENCE: 87
aguacaaugg cgc                                                          13

<210> SEQ ID NO 88
<211> LENGTH: 14
<212> TYPE: RNA
<213> ORGANISM: artificial sequence
<220> FEATURE:
<223> OTHER INFORMATION: IK10L, IKAP ExSpeU1s binding region within the
      IKBKAP intron 20 binding sequence.

<400> SEQUENCE: 88
gcaaacagua caau                                                         14

<210> SEQ ID NO 89
<211> LENGTH: 14
<212> TYPE: RNA
<213> ORGANISM: artificial sequence
<220> FEATURE:
<223> OTHER INFORMATION: IK12, IKAP ExSpeU1s binding regions within the
      IKBKAP intron 20.

<400> SEQUENCE: 89
ucgcaaacag uaca                                                         14

<210> SEQ ID NO 90
<211> LENGTH: 12
<212> TYPE: RNA
<213> ORGANISM: artificial sequence
<220> FEATURE:
<223> OTHER INFORMATION: IK19, IKAP ExSpeU1s binding regions within the
      IKBKAP intron 20.

<400> SEQUENCE: 90
cuagucgcaa ac                                                           12

<210> SEQ ID NO 91
<211> LENGTH: 13
<212> TYPE: DNA
<213> ORGANISM: Homo sapiens

<400> SEQUENCE: 91
gcgccattgt act                                                          13

<210> SEQ ID NO 92
<211> LENGTH: 14
<212> TYPE: DNA
<213> ORGANISM: Homo sapiens
```

```
<400> SEQUENCE: 92
attgtactgt ttgc                                                         14

<210> SEQ ID NO 93
<211> LENGTH: 14
<212> TYPE: DNA
<213> ORGANISM: Homo sapiens

<400> SEQUENCE: 93
tgtactgttt gcga                                                         14

<210> SEQ ID NO 94
<211> LENGTH: 12
<212> TYPE: DNA
<213> ORGANISM: Homo sapiens

<400> SEQUENCE: 94
gtttgcgact ag                                                           12

<210> SEQ ID NO 95
<211> LENGTH: 54
<212> TYPE: DNA
<213> ORGANISM: Homo sapiens

<400> SEQUENCE: 95
caagtaagtg ccattgtact gtttgcgact agttagcttg tgatttatgt gtga             54

<210> SEQ ID NO 96
<211> LENGTH: 17
<212> TYPE: RNA
<213> ORGANISM: Artificial Sequence
<220> FEATURE:
<223> OTHER INFORMATION: SMN_SH 40, binding sequence, recognition
      sequence (U1-SR) in the gene for the modified U1-snRNAs for the
      correction of the splicing defect of exon 7 in the SMN2 gene

<400> SEQUENCE: 96
caaaccauaa aguuuua                                                      17

<210> SEQ ID NO 97
<211> LENGTH: 42
<212> TYPE: DNA
<213> ORGANISM: Artificial Sequence
<220> FEATURE:
<223> OTHER INFORMATION: U1ex7SMN sh25 dir, oligonucleotide for U1 SMN.

<400> SEQUENCE: 97
gatctcatat acaaaagtaa gattcagcag gggagatacc at                          42

<210> SEQ ID NO 98
<211> LENGTH: 42
<212> TYPE: DNA
<213> ORGANISM: Artificial Sequence
<220> FEATURE:
<223> OTHER INFORMATION: U1ex7SMN sh25 rev, Oligonucleotides for U1 SMN

<400> SEQUENCE: 98
gatcatggta tctcccctgc tgaatcttac ttttgtatat ga                          42

<210> SEQ ID NO 99
<211> LENGTH: 43
<212> TYPE: DNA
<213> ORGANISM: Artificial Sequence
<220> FEATURE:
```

```
<223> OTHER INFORMATION: U1ex7SMN sh37 dir, Oligonucleotides for U1 SMN

<400> SEQUENCE: 99
gatctcataa accataaagt tttacaagca ggggagatac cat                    43

<210> SEQ ID NO 100
<211> LENGTH: 43
<212> TYPE: DNA
<213> ORGANISM: Artificial Sequence
<220> FEATURE:
<223> OTHER INFORMATION: U1ex7SMN sh37 rev, Oligonucleotides for U1 SMN

<400> SEQUENCE: 100
gatcatggta tctcccctgc ttgtaaaact ttatggttta tga                    43

<210> SEQ ID NO 101
<211> LENGTH: 42
<212> TYPE: DNA
<213> ORGANISM: Artificial Sequence
<220> FEATURE:
<223> OTHER INFORMATION: U1ex7SMN sh37 rev, Oligonucleotides for U1 SMN

<400> SEQUENCE: 101
gatctcatac aaaccataaa gttttagcag gggagatacc at                     42

<210> SEQ ID NO 102
<211> LENGTH: 42
<212> TYPE: DNA
<213> ORGANISM: Artificial Sequence
<220> FEATURE:
<223> OTHER INFORMATION: U1ex7SMN sh40 rev, Oligonucleotides for U1 SMN

<400> SEQUENCE: 102
gatcatggta tctcccctgc taaaacttta tggtttgtat ga                     42

<210> SEQ ID NO 103
<211> LENGTH: 17
<212> TYPE: DNA
<213> ORGANISM: Homo sapiens

<400> SEQUENCE: 103
taaaacttta tggtttg                                                 17

<210> SEQ ID NO 104
<211> LENGTH: 72
<212> TYPE: RNA
<213> ORGANISM: Homo sapiens

<400> SEQUENCE: 104
aaggaguaag ucugccagca uuaugaaagu gaaucuuacu uuuguaaaac uuuaugguuu  60
guggaaaaca aa                                                      72
```

What is claimed is:

1. A modified human U1snRNA molecule, capable of correcting the skipping of an exon caused by a mutation localized in the sequence comprised between 50 base pairs upstream and 20 base pairs downstream of an exon, wherein a portion of a single-stranded nucleotide sequence of the 5' region of the wild-type human U1snRNA is replaced by a single-stranded nucleotide binding sequence,
   wherein the nucleotide binding sequence is selected from the group consisting of: uggcgcuua, aauggcgcu, aguacaauggcgc (SEQ ID NO: 87), gcaaacaguacaau (SEQ ID NO: 88), ucgcaaacaguaca (SEQ ID NO: 89), gcaaacagu, cuagucgcaaac (SEQ ID NO: 90), uacaaaaguaagauuca (SEQ ID NO: 83), aaaccauaaaguuuuacaa (SEQ ID NO: 84) and caaaccauaaaguuuua (SEQ ID NO: 96).

2. An isolated gene encoding for a modified human U1snRNA molecule according to claim 1.

3. The isolated gene according to claim 2, comprising a promoter sequence and a polyadenylation signal sequence.

4. The isolated gene according to claim 3, wherein the promoter is the endogenous promoter of the gene encoding for human U1 snRNA.

5. An expression vector comprising an isolated gene according to claim 2.

6. The expression vector according to claim 5, which is an adeno-associated viral vector.

7. A pharmaceutical composition comprising a modified human U1snRNA molecule according to claim 1, and a pharmaceutically acceptable carrier.

8. A pharmaceutical composition comprising an isolated gene according to claim 2, and a pharmaceutically acceptable carrier.

9. A pharmaceutical composition comprising an expression vector according to claim 5, and a pharmaceutically acceptable carrier.

10. A method of treating familial dysautonomia caused by, or associated with, exon skipping, the method comprising administering the modified human U1snRNA molecule according to claim 1, to a patient in need thereof, thereby treating familial dysautonomia caused by, or associated with, exon skipping.

11. A method of treating familial dysautonomia caused by, or associated with, exon skipping, the method comprising administering the isolated gene according to claim 2, to a patient in need thereof, thereby treating familial dysautonomia caused by, or associated with, exon skipping.

12. A method of treating familial dysautonomia caused by, or associated with, exon skipping, the method comprising administering the expression vector according to claim 5, to a patient in need thereof, thereby treating familial dysautonomia caused by, or associated with, exon skipping.

13. A method of treating spinal muscular atrophy caused by, or associated with, exon skipping, the method comprising administering the modified human U1snRNA molecule according to claim 1, to a patient in need thereof, thereby treating spinal muscular atrophy caused by, or associated with, exon skipping.

14. A method of treating spinal muscular atrophy caused by, or associated with, exon skipping, comprising administering the isolated gene according to claim 2, to a patient in need thereof, thereby treating spinal muscular atrophy caused by, or associated with, exon skipping.

15. A method of treating spinal muscular atrophy caused by, or associated with, exon skipping, the method comprising administering the expression vector according to claim 5, to a patient in need thereof, thereby treating spinal muscular atrophy caused by or associated with exon skipping.

16. An in vitro method to restore in a cultured cell the correct splicing of a target gene of therapeutic interest bearing a mutation which induces exon skipping, comprising transfecting the cultured cell with an expression vector according to claim 5, in order to upregulate a function of and/or the expression of the target gene of therapeutic interest in the cultured cell, wherein the target gene of therapeutic interest is the SMN gene or the IKBKAP gene.

* * * * *